(12) United States Patent
Morimoto et al.

(10) Patent No.: US 10,801,971 B2
(45) Date of Patent: Oct. 13, 2020

(54) X-RAY PHASE CONTRAST IMAGING WITH FOURIER TRANSFORM DETERMINATION OF GRATING DISPLACEMENT

(71) Applicant: Shimadzu Corporation, Kyoto (JP)

(72) Inventors: Naoki Morimoto, Kyoto (JP); Taro Shirai, Kyoto (JP); Takahiro Doki, Kyoto (JP); Satoshi Sano, Kyoto (JP); Akira Horiba, Kyoto (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 315 days.

(21) Appl. No.: 15/958,048

(22) Filed: Apr. 20, 2018

(65) Prior Publication Data

US 2018/0306734 A1    Oct. 25, 2018

(30) Foreign Application Priority Data

Apr. 20, 2017 (JP) .................. 2017-084030
Feb. 28, 2018 (JP) .................. 2018-035646

(51) Int. Cl.
  *G01N 23/041*    (2018.01)
  *A61B 6/00*      (2006.01)
  (Continued)

(52) U.S. Cl.
  CPC ......... *G01N 23/041* (2018.02); *A61B 6/4035* (2013.01); *A61B 6/484* (2013.01);
  (Continued)

(58) Field of Classification Search
  CPC ........ G01N 23/00; G01N 23/02; G01N 23/04; G01N 23/041; G01N 23/083; G01N 23/20; G01N 23/20008; G01N 23/20075; G01N 2021/4173; G01N 2021/4186; G01N 2021/45; G01N 2223/00; G01N 2223/05; G01N 2223/064; G01N 2223/1016; G01N 2223/30; G01N 2223/302; G01N 2223/303; G01N 2223/304; G01N 2223/306; G01N 2223/313; G01N 2223/32; G01N 2223/321; G01N 2223/40; G01N 2291/01;
  (Continued)

(56) References Cited

U.S. PATENT DOCUMENTS

2012/0163537 A1    6/2012  Iwakiri et al.
2014/0010344 A1*   1/2014  Nagatsuka ............ A61B 6/06
                                                378/37
(Continued)

FOREIGN PATENT DOCUMENTS

WO    2014/030115 A1    2/2014

OTHER PUBLICATIONS

Partial European Search Report dated Jul. 30, 2018 for corresponding European patent application No. 18000380.8.

*Primary Examiner* — Anastasia Midkiff
(74) *Attorney, Agent, or Firm* — Muir Patent Law, PLLC

(57) ABSTRACT

An X-ray phase contrast imaging system includes an X-ray source, a detector, a plurality of gratings including a first grating and a second grating, and a grating positional displacement acquisition section configured to obtain a positional displacement of the grating based on a Fourier transform image obtained by Fourier transforming an interference fringe image detected by the detector.

12 Claims, 15 Drawing Sheets

(51) Int. Cl.
*G01N 23/20* (2018.01)
*G01N 23/20008* (2018.01)
*G06K 9/32* (2006.01)
*G21K 1/06* (2006.01)
*G06K 9/20* (2006.01)
*G01N 21/41* (2006.01)
*G01T 1/29* (2006.01)
*G06T 7/262* (2017.01)

(52) U.S. Cl.
CPC . *G01N 23/20008* (2013.01); *G01N 23/20075* (2013.01); *G06K 9/2036* (2013.01); *G06K 9/3208* (2013.01); *G21K 1/06* (2013.01); *A61B 6/5211* (2013.01); *A61B 6/547* (2013.01); *A61B 6/584* (2013.01); *G01N 2021/4186* (2013.01); *G01N 2223/064* (2013.01); *G01N 2223/302* (2013.01); *G01N 2223/313* (2013.01); *G01N 2223/32* (2013.01); *G01T 1/2914* (2013.01); *G06K 2009/2045* (2013.01); *G06T 7/262* (2017.01); *G06T 2207/20056* (2013.01); *G21K 2207/005* (2013.01)

(58) Field of Classification Search
CPC .... G01N 2291/012; G21K 1/06; G21K 1/067; G21K 1/10; G21K 2201/00; G21K 2201/06; G21K 2201/067; G21K 2207/00; G21K 2207/005; G01T 1/29; G01T 1/2914; G06K 9/00496; G06K 9/00503; G06K 9/0051; G06K 9/20; G06K 9/2036; G06K 9/32; G06K 9/3208; G06K 9/3216; G06K 9/34; G06K 9/40; G06K 9/522; G06K 2009/2045; G06K 2009/3291; G06T 5/00; G06T 5/001; G06T 5/002; G06T 7/174; G06T 7/262; G06T 2207/10; G06T 2207/10116; G06T 2207/10141; G06T 2207/20; G06T 2207/20048; G06T 2207/20056; G06T 2207/20182; G06T 2207/20221; A61B 2560/02; A61B 2560/0223
See application file for complete search history.

(56) References Cited

U.S. PATENT DOCUMENTS

2014/0126690 A1    5/2014  Yamaguchi
2015/0182178 A1*  7/2015  Baturin ................ A61B 6/4035
                                                   378/36
2015/0243397 A1*  8/2015  Yun ......................... H01J 35/08
                                                   378/36

* cited by examiner

First Embodiment

First Embodiment

First Embodiment

First Embodiment

First Embodiment

First Embodiment

First Embodiment

First Embodiment

First Embodiment

First Embodiment

First Embodiment

First Embodiment

First Embodiment

First Embodiment

Second Embodiment

Second Embodiment

Second Embodiment

Modification of Second Embodiment

X-RAY PHASE CONTRAST IMAGING WITH FOURIER TRANSFORM DETERMINATION OF GRATING DISPLACEMENT

CROSS-REFERENCE TO RELATED APPLICATIONS

The priority application number JP2017-084030, entitled "X-ray phase contrast imaging system", filed on Apr. 20, 2017, invented by Naoki Morimoto, Taro Shirai, Takahiro Doki, Satoshi Sano, and Akira Horiba, and JP2018-035646, entitled "X-ray phase contrast imaging system", filed on Feb. 28, 2018, invented by Naoki Morimoto, Taro Shirai, Takahiro Doki, Satoshi Sano, and Akira Horiba, upon which this patent application is based are hereby incorporated by reference.

BACKGROUND OF THE INVENTION

Field of the Invention

The present invention relates to an X-ray phase contrast imaging system.

Description of the Background Art

Conventionally, an X-ray phase contrast imaging system is known. Such an X-ray phase contrast imaging system is disclosed in, for example, WO 2014/030115.

WO 2014/030115 discloses an X-ray phase contrast imaging system for imaging a phase contrast image by detecting a moire fringe generated by translating a source grating. The X-ray phase contrast imaging system disclosed in WO 2014/030115 includes an X-ray phase contrast imaging apparatus equipped with an X-ray source, a source grating, a phase grating, an absorption grating, and a detector. This X-ray phase contrast imaging apparatus is a so-called Talbot Lau interferometer.

Further, the X-ray phase contrast imaging system disclosed in WO 2014/030115 is configured to capture a phase contrast image by calculating a translational signal that translates a source grating so that a moire fringe has a predetermined period and translating the source grating based on the calculated translational signal.

Here, in a Talbot Lau interferometer, an X-ray that has passed through a source grating is irradiated to a phase grating. The irradiated X-ray diffracts as it passes through the phase grating and forms a self-image of the phase grating at a position separated by a predetermined distance (Talbot distance). The period of the self-image of the formed phase grating is so small that the self-image cannot be detected by a general-purpose detector. Therefore, in a Talbot Lau interferometer, an absorption grating is placed at the position where a self-image of a phase grating is formed to form a moire fringe which can be detected even by a general-purpose detector. Further, in a Talbot Lau interferometer, by performing a plurality of image capturing (fringe scanning image capturing) while translating any one of gratings in the periodic direction of the grating, it is possible to detect a slight change of the self-image and obtain a phase contrast image.

However, in the Talbot Lau interferometer described in WO 2014/030115, when the relative position between the phase grating and the absorption grating is displaced from the design position, an unintended moire fringe is generated. In this case, since the unintended moire fringe is detected by the detector, there is a disadvantage that an artifact (virtual image) is generated in the captured image due to the unintended moire fringe.

Note that the "unintended moire fringe" denotes a moire fringe caused by the displacement of the relative position between a phase grating and an absorption grating, which is generated in a state in which no object is arranged. Further, the "artifact (virtual image)" denotes disorder of a phase contrast image or degradation of the image quality of the phase contrast image, which is generated due to the unintended moire fringe.

Therefore, in a Talbot Lau interferometer, the relative position between the phase grating and the absorption grating is adjusted before performing image capturing. However, in order to adjust the positional displacement of the grating, the measurer should judge the multi-directional positional displacements, such as, e.g., the translation direction and the rotational direction, from the shape of the complex moire fringe by the visual inspection. For this reason, there are problems that the measurer is required to have knowledge and/or experience and it takes time to adjust the grating positioning.

The present invention has been made to solve the aforementioned problems, and one object of the present invention is to provide an X-ray phase contrast imaging system capable of adjusting a positional displacement of a grating without depending on knowledge and/or experience of a measurer and capable of shortening an adjustment time.

SUMMARY OF THE INVENTION

In order to achieve the aforementioned object, an X-ray phase contrast imaging system according to one aspect of the present invention includes: an X-ray source; a detector configured to detect an X-ray irradiated from the X-ray source; a plurality of gratings disposed between the X-ray source and the detector, the plurality of gratings including a first grating for forming a self-image by being irradiated by the X-ray from the X-ray source and a second grating for forming an interference fringe with the self-image of the first grating by being irradiated by the X-ray that has passed through the first grating; and a grating positional displacement acquisition section configured to acquire a positional displacement of the grating based on a Fourier transform image obtained by Fourier transforming an interference fringe image detected by the detector.

Here, when the relative position between the first grating and the second grating is displaced from the design position, an unintended moire fringe is generated. Therefore, in the Fourier transform image, in addition to the peaks due to the self-image of the first grating, peaks due to the unintended moire fringe are generated.

According to the present invention, since the aforementioned grating positional displacement acquisition section acquires the positional displacement of the grating based on the Fourier transform image, the position adjustment of the grating can be performed based on the obtained positional displacement of the grating. Therefore, it is possible to adjust the positional displacement of the grating without depending on knowledge and/or experience of a measurer and shorten the adjustment time.

In the X-ray phase contrast imaging system according to the aforementioned one aspect of the present invention, it is preferably configured such that the X-ray phase contrast imaging system further include an adjustment mechanism configured to adjust the positional displacement of at least either one of the first grating and the second grating, wherein the adjustment mechanism is configured to correct the positional displacement of the grating based on the positional displacement of the grating acquired by the grating positional displacement acquisition section.

With this configuration, it becomes possible to automatically correct the positional displacement of the grating by the adjustment mechanism based on the positional displacement of the grating obtained by the grating positional displacement acquisition section. Therefore, the positional displacement of the grating can be more easily adjusted without depending on knowledge and/or experience of a measurer. Further, it becomes possible to automatically correct the positional displacement of the grating by the adjustment mechanism, so the adjustment time can be further shortened.

In the X-ray phase contrast imaging system according to the aforementioned one aspect of the present invention, it is preferably configured such that the grating positional displacement acquisition section be configured to acquire the positional displacement of the grating based on at least either one of a peak-to-peak distance and a peak magnitude of the Fourier transform image.

Here, note that the distance between peaks of the Fourier transform image denotes an amount representing the positional displacement of the grating in the irradiation direction of the X-ray described later or the positional displacement of the grating in the rotational direction about the optical axis direction of the X-ray. Further, note that the magnitude of the peak of the Fourier transform image does not denote the intensity of the frequency component to be detected but the magnitude of the peak in the Fourier image. Also note that the magnitude of the peak of the Fourier transform image denotes an amount representing the positional displacement of the grating which will be described later in the rotational direction about the central axis of the vertical direction orthogonal to the optical axis direction of the X-ray or the positional displacement of the grating in the rotational direction about the central axis of the horizontal direction orthogonal to the optical axis direction.

With this configuration, the positional displacement of the grating can be acquired by subjecting the Fourier transform image to image processing. As a result, the positional displacement of the grating can be automatically acquired without the measurer's visual confirmation of the moire fringe.

In the X-ray phase contrast imaging system according to the aforementioned one aspect of the present invention, it is preferably configured such that the grating positional displacement acquisition section be configured to acquire a positional displacement of the first grating or the second grating in an optical axis direction of the X-ray or a positional displacement of the first grating or the second grating in a rotational direction about the optical axis direction of the X-ray based on a distance between a zero-order peak and a first-order peak in the Fourier transform image.

With such a configuration, the positional displacement of the first grating or the second grating in the optical axis direction of the X-ray can be grasped by replacing the positional displacement with the magnitude of the distance between the zero-order peak and the first-order peak of the Fourier transform image. As a result, by adjusting the position of the grating so that the distance between the zero-order peak and the first-order peak of the Fourier transform image becomes smaller, the positional displacement of the first grating or the second grating in the optical axis direction of the X-ray can be easily adjusted. Alternatively, the positional displacement of the first grating or the second grating in the rotational direction about the optical axis direction of the X-ray can be grasped by replacing the positional displacement with the magnitude of the distance between the zero-order peak and the first-order peak of the Fourier transform image. As a result, by adjusting the position of the grating so that the distance between the zero-order peak and the first-order peak of the Fourier transform image becomes smaller, the positional displacement of the first grating or the second grating in the rotational direction about the optical axis direction of the X-ray can be easily adjusted.

In the X-ray phase contrast imaging system according to the aforementioned one aspect of the present invention, it is preferably configured such that the grating positional displacement acquisition section be configured to acquire a magnitude of the positional displacement of the grating based on the distance between the zero-order peak and the first-order peak in the Fourier transform image.

With this configuration, the magnitude of the positional displacement of the grating can be obtained. As a result, the positional displacement of the first grating or the second grating can be more easily and accurately adjusted by adjusting the position of the grating considering the magnitude of the acquired positional displacement as a correction amount.

In the X-ray phase contrast imaging system according to the aforementioned one aspect of the present invention, it is preferably configured such that the grating positional displacement acquisition section be configured to acquire the positional displacement of the first grating or the second grating in a rotational direction about a central axis of a vertical direction or a horizontal direction orthogonal to an optical axis direction of the X-ray of the first grating or the second grating based on a magnitude of a first-order peak in the Fourier transform image.

With this configuration, the positional displacement of the first grating or the second grating in the rotational direction about the central axis of the vertical direction orthogonal to the optical axis direction of the X-ray of the first grating or the second grating can be grasped by replacing the positional displacement with the magnitude of the first-order peak of the Fourier transform image. As a result, by adjusting the grating so that the magnitude of the first-order peak of the Fourier transform image becomes small, it is possible to easily adjust the positional displacement of the first grating or the second grating in the rotational direction about the central axis of the vertical direction orthogonal to the optical axis direction of the X-ray of the first grating or the second grating.

Alternatively, the positional displacement of the first grating or the second grating in the rotational direction about the central axis of the horizontal direction orthogonal to the optical axis direction of the X-ray of the first grating or the second grating can be grasped by replacing the positional displacement with the magnitude of the first-order peak of the Fourier transform image. As a result, by adjusting the grating so that the magnitude of the first-order peak of the Fourier transform image becomes small, it is possible to easily adjust the positional displacement of the first grating or the second grating in the rotational direction about the central axis of the horizontal direction orthogonal to the optical axis direction of the X-ray of the first grating or the second grating.

In the X-ray phase contrast imaging system according to the aforementioned one aspect of the present invention, it is preferably configured such that the grating positional displacement acquisition section be configured to acquire presence or absence of a positional displacement of the grating based on the magnitude of the first-order peak in the Fourier transform image.

With this configuration, it is possible to automatically judge the presence or absence of the positional displacement of the first grating or the second grating by subjecting the Fourier transform image to image processing.

In this case, it is preferable that the grating positional displacement acquisition section is configured to acquire a rotation amount that a magnitude of the first-order peak in the Fourier transform image becomes a minimum value or near the minimum value as a positional displacement amount based on a plurality of Fourier transform images captured by rotating either one of the first grating and the second grating.

With such a configuration, it is possible to acquire a relative position of the grating where the positional displacement of the grating becomes as small as possible based on a plurality of Fourier transform images. As a result, the positional displacement of the first grating or the second grating can be easily and accurately adjusted.

In the X-ray phase contrast imaging system according to the aforementioned one aspect of the present invention, it is preferably configured such that the X-ray phase contrast imaging system further include a noise elimination processing section configured to eliminate frequency noise from the image detected by the detector before performing the Fourier transforming.

With this configuration, it is possible to eliminate the artifact (virtual image) due to the analysis of a finite space when performing Fourier transform and/or the artifact (virtual image) derived from the detector before performing the Fourier transform. As a result, it is possible to detect peaks due to the positional displacement of the grating obtained by the Fourier transform more accurately.

In the X-ray phase contrast imaging system according to the aforementioned one aspect of the present invention, it is preferably configured such that the X-ray phase contrast imaging system further include an image processing section configured to eliminate noise generated in the Fourier transform image by using a Fourier transform reference image previously obtained by Fourier transforming the interference fringe image.

With this configuration, it is possible to eliminate noise generated in the Fourier transform image, which enables accurate acquisition of the position and/or the magnitude of the first-order peak. As a result, it becomes possible to detect the peaks due to the positional displacement of the grating obtained by the Fourier transform more accurately, which in turn can enhance the accuracy of adjusting the positional displacement of the grating.

Note that the noise generated in the Fourier transform image denotes noise generated in the Fourier transform image due to, for example, a pixel defect of the detector, sensitivity unevenness due to the irradiation direction of the X-ray, or a defect of the grating.

In the X-ray phase contrast imaging system according to the aforementioned one aspect of the present invention, it is preferably configured such that the image processing section be configured to eliminate the noise by subtracting the Fourier transform reference image from the Fourier transform image.

With this configuration, unlike random noise, it is possible to easily eliminate the noise of the Fourier transform image that is hardly changes temporally.

In the X-ray phase contrast imaging system according to the aforementioned one aspect of the present invention, it is preferably configured such that the Fourier transform reference image be an image which is different from the Fourier transform image in a position of the first-order peak or an image obtained by eliminating the first-order peak of the Fourier transform image.

By using such a Fourier transform reference image, when eliminating the noise of the Fourier transform image, the first-order peak of the Fourier transform image can be suppressed from being eliminated together with the noise by the first-order peak of the Fourier transform reference image. As a result, the noise of the Fourier transform image can be eliminated regardless of the position of the first-order peak in the Fourier transform image.

DESCRIPTION OF PREFERRED EMBODIMENTS

Hereinafter, embodiments of the present invention will be described with reference to the drawings.

First Embodiment

With reference to FIG. 1 to FIG. 16, a configuration of an X-ray phase contrast imaging system 100 according to a first embodiment of the present invention will be described.
(Configuration of X-Ray Phase Contrast Imaging System)

Figure 1:
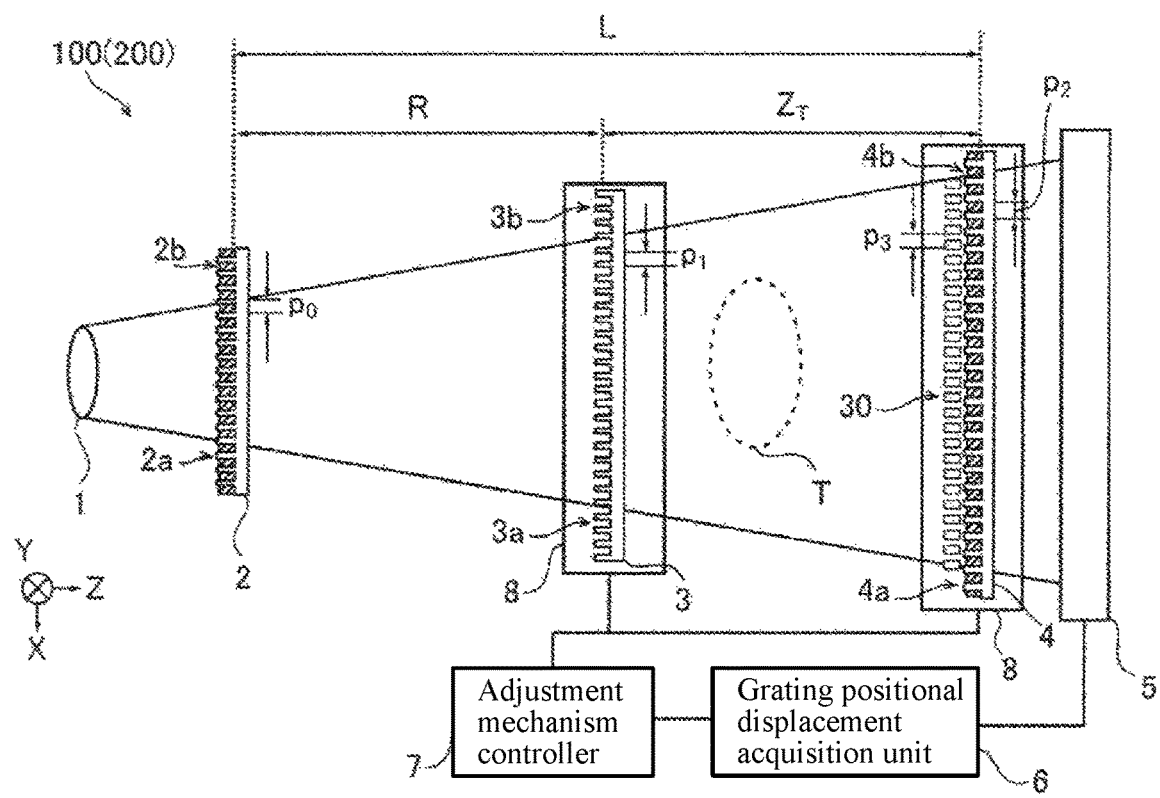
FIG. 1 is a diagram showing an overall structure of an X-ray phase contrast imaging system according to a first embodiment of the present invention.

As shown in FIG. 1, the X-ray phase contrast imaging system 100 is an apparatus for imaging the inside of the object T by using the phase contrast of the X-ray that has passed through the object T. Further, the X-ray phase contrast imaging system 100 is an apparatus for imaging the inside of the object T utilizing a Talbot effect. For example, in nondestructive inspection applications, the X-ray phase contrast imaging system 100 can be used for imaging an inside of an object T as an object. Further, in medical applications, for example, the X-ray phase contrast imaging system 100 can be used for imaging an inside of an object T as a living body.

FIG. 1 is a top view of the X-ray phase contrast imaging system 100. As shown in FIG. 1, the X-ray phase contrast imaging system 100 is provided with an X-ray source 1, a third grating 2, a first grating 3, a second grating 4, a detector 5, a grating positional displacement acquisition unit 6, an adjustment mechanism controller 7, and adjustment mechanisms 8.

In this specification, the direction from the X-ray source 1 to the third grating 2 is defined as a Z-direction. Further, the left-right direction within the plane orthogonal to the Z-direction is defined as an X-direction. Further, the vertical direction within the plane orthogonal to the Z-direction is defined as a Y-direction. The X-direction is an example of the "horizontal direction orthogonal to the optical axis direction of the X-ray" recited in claims. The Y-direction is an example of the "vertical direction orthogonal to the optical axis direction of the X-ray" recited in claims. The Z-direction is an example of the "optical axis direction of the X-ray" recited in claims.

The X-ray source 1 is configured to generate an X-ray by being applied by a high voltage and irradiate the generated X-ray in the Z-direction.

The third grating 2 includes a plurality of X-ray transmission portions 2a and X-ray absorption portions 2b arranged in the X-direction at a predetermined period (pitch) p0. The X-ray transmission portion 2a and the X-ray absorption portion 2b are each configured to extend in the Y-direction.

The third grating 2 is arranged between the X-ray source 1 and the first grating 3 and is configured to be irradiated by the X-ray from the X-ray source 1. The third grating 2 is configured to make the X-ray that have passed through the X-ray transmission portions 2a as line light sources each corresponding to the position of each X-ray transmission portion 2a. With this, the third grating 2 can enhance the coherence of the X-ray irradiated from the X-ray source 1.

The first grating 3 includes a plurality of slits 3a and X-ray phase change portions 3b arranged in the X-direction at a predetermined period (pitch) p1. The slits 3a and the X-ray phase change portions 3b are each formed so as to extend in the Y-direction.

The first grating 3 is arranged between the third grating 2 and the second grating 4, and is irradiated by the X-ray that has passed through the third grating 2. The first grating 3 is provided to form a self-image 30 by a Talbot effect. When an X-ray with coherence passes through the grating where the slits are formed, the image of the grating (self-image 30) is formed at a position away from the grating by a predetermined distance (Talbot distance). This is called a Talbot effect.

The second grating 4 includes a plurality of X-ray transmission portions 4a and X-ray absorption portions 4b arranged in the X-direction at a predetermined period (pitch) $p_2$. The third grating 2, the first grating 3, and the second grating 4 are gratings having different roles, respectively, but the X-ray transmission portion 2a, the slit 3a, and the X-ray transmission portion 4a respectively transmit the X-ray. Further, the X-ray absorption portion 2b and the X-ray absorption portion 4b respectively play a role of shielding the X-ray, and the X-ray phase change portion 3b changes the phase of the X-ray by the difference of the refractive index with the slit 3a.

The second grating 4 is arranged between the first grating 3 and the detector 5, and is irradiated by the X-ray that has passed through the first grating 3. Further, the second grating 4 is disposed at a position away from the first grating 3 by the Talbot distance. The second grating 4 interferes with the self-image 30 of the first grating 3 to form a moire fringe 12 (see FIG. 6A) on the detection surface of the detector 5.

The detector 5 is configured to detect the X-ray, convert the detected X-ray into an electric signal, and read out the converted electric signal as an image signal. The detector 5 is, for example, an FPD (Flat Panel Detector). The detector 5 is composed of a plurality of conversion elements (not shown) and a plurality of pixel electrodes (not shown) arranged on the plurality of conversion elements. The plurality of conversion elements and pixel electrodes are arranged in an array manner in the X-direction and Y-direction at a predetermined period (pixel pitch). Also, the detector 5 is configured to output the acquired image signal to the grating positional displacement acquisition unit 6.

Figure 2:
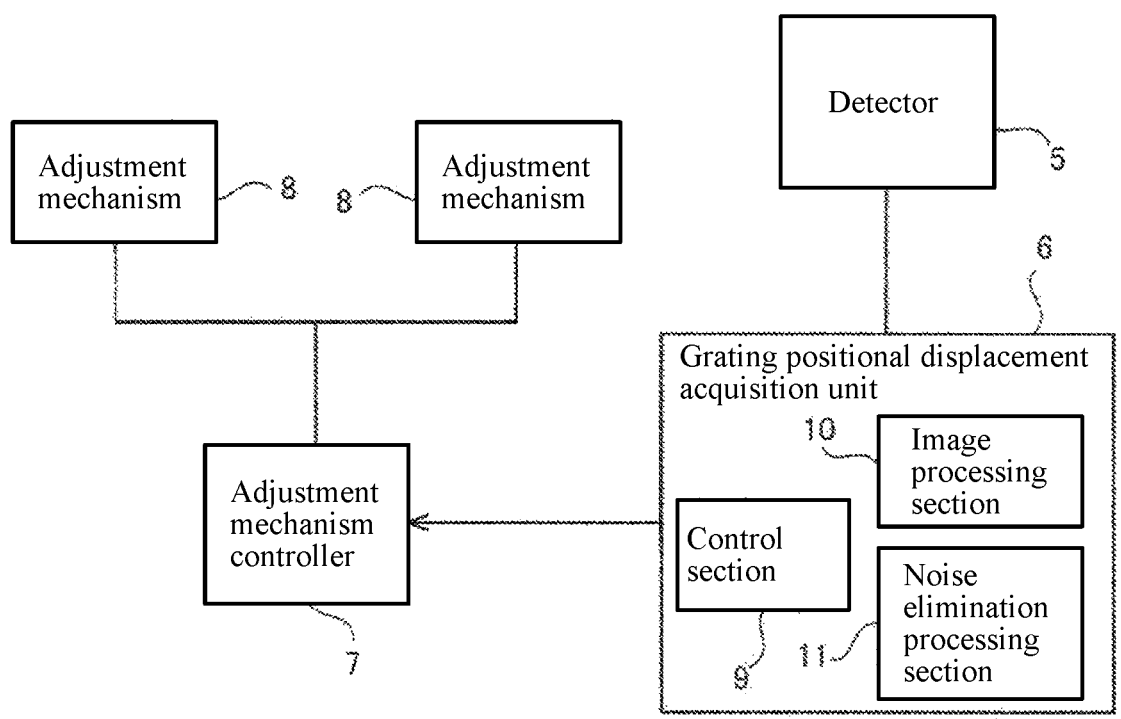
FIG. 2 is a block diagram showing a configuration of the X-ray phase contrast imaging system according to the first embodiment of the present invention.

As shown in FIG. 2, the grating positional displacement acquisition unit 6 includes a control section 9, an image processing section 10 and a noise elimination processing section 11. The grating positional displacement acquisition unit 6 may be embodied by a computer including a CPU configured by software. The control section 9, the image processing section 10 and the noise elimination processing section 11 of the grating positional displacement acquisition unit 6 may be formed as a CPU configured by one or more software modules (e.g., code segments) that may be separate or combined (e.g., share various software and/or hardware resources). The control section 9 is configured to Fourier transform the image signal output from the detector 5 to generate a Fourier transform image 14 (see FIG. 9). Further, the control section 9 is configured to acquire the positional displacement of the first grating 3 or the second grating 4 and output it to the adjustment mechanism controller 7.

The image processing section 10 is configured to acquire the distance between the peaks and the magnitudes of the peaks in the Fourier transform image 14 generated by the control section 9.

Note that the magnitude of the peak denotes the magnitude of the peak in the Fourier transform image 14 and is determined by the dispersion degree of the frequency peaks after Fourier transforming. Further note that the magnitude of the peak is determined by the width of the frequency peak from the maximum amplitude of the frequency peak to the predetermined amplitude after Fourier transforming. In the first embodiment, the predetermined width is set to the width of the frequency peak (so-called half-value width) up to 50% of the maximum amplitude as the magnitude of the peak.

Further, the noise elimination processing section 11 is configured to eliminate the frequency noise from the image detected by the detector 5 before Fourier transforming. Specifically, the noise elimination processing section 11 is configured to perform any one or more of filtering by a window function, a dark correction, a gain correction, and a defect correction. In the first embodiment, the noise elimination processing section 11 is configured to perform all of the filtering and corrections.

The filtering by a window function denotes processing of eliminating the discontinuity of the boundary by multiplying actual data of the acquired image by a specific window function. With this, it is possible to eliminate the artifact (virtual image) due to the analysis of the finite space from the image after Fourier transforming. The specific window function is, for example, a hanning function or a hamming function.

Further, the dark correction denotes processing of subtracting an image (dark image) captured in a state of not being irradiated by an X-ray from an image captured by being irradiated by an X-ray. With this, it is possible to eliminate the artifact (virtual image) derived from the detector 5 from the image after Fourier transforming.

Moreover, the gain correction denotes processing of dividing an image (air image) captured by being irradiated by the X-ray without arranging a grating from an image captured by arranging a grating. With this, it is possible to eliminate the artifact (virtual image) derived from the detector 5 from the image after Fourier transforming.

Further, the defect correction denotes processing of correcting the defective portion in which the sensitivity of the detector 5 is significantly lowered by averaging processing with surrounding pixels. With this, it is possible to eliminate the artifact (virtual image) derived from the detector 5 from the image after Fourier transforming.

In some examples, control section 9 and the noise elimination processing section 11 each include, for example, a CPU (Central Processing Unit). Further, the image processing section 10 includes, for example, a CPU or a GPU (Graphics Processing Unit).

The adjustment mechanism controller 7 is configured to output a signal for correcting the positional displacement of the first grating 3 or the second grating 4 to the adjustment mechanisms 8 based on the positional displacement of the first grating 3 or the second grating 4 output from the grating positional displacement acquisition unit 6. The adjustment mechanism controller 7 includes, for example, a CPU.

The adjustment mechanism 8 is configured to correct the positional displacement of the first grating 3 or the second grating 4 based on the signal for correcting the positional displacement output from the adjustment mechanism controller 7.

Figure 3:
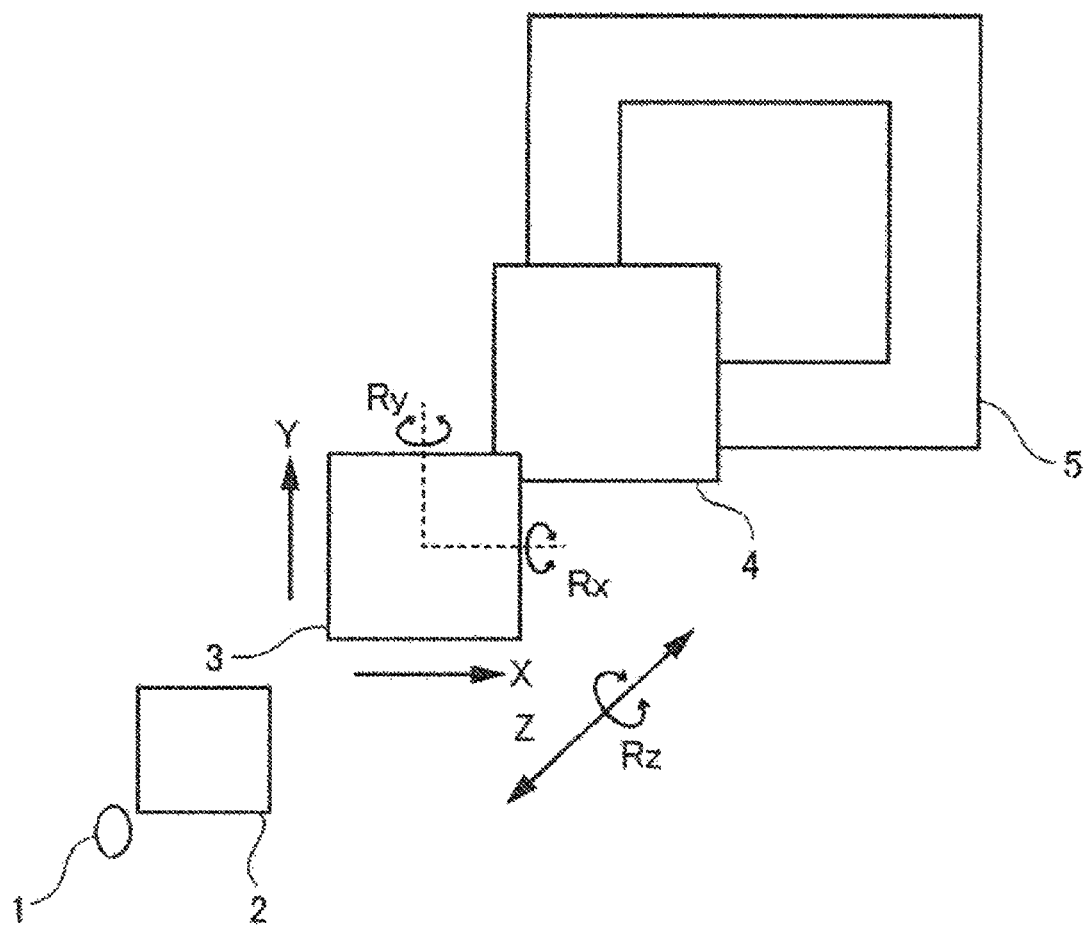
FIG. 3 is a perspective view for explaining the positional displacement of the grating of the X-ray phase contrast imaging system according to the first embodiment of the present invention.

Next, with reference to FIG. 3 and FIG. 4, the configuration in which the adjustment mechanism 8 adjusts the positional displacement of the first grating 3 or the second grating 4 will be described. As shown in FIG. 3, the positional displacement of the first grating 3 or the second grating 4 mainly includes a positional displacement in the Z-direction, a positional displacement in the rotational direction Rz about the Z-direction axis, a positional displacement in the rotational direction Rx about the central axis of the X-direction, and a positional displacement in the rotational direction Ry about the central axis of the Y-direction.

Figure 4:
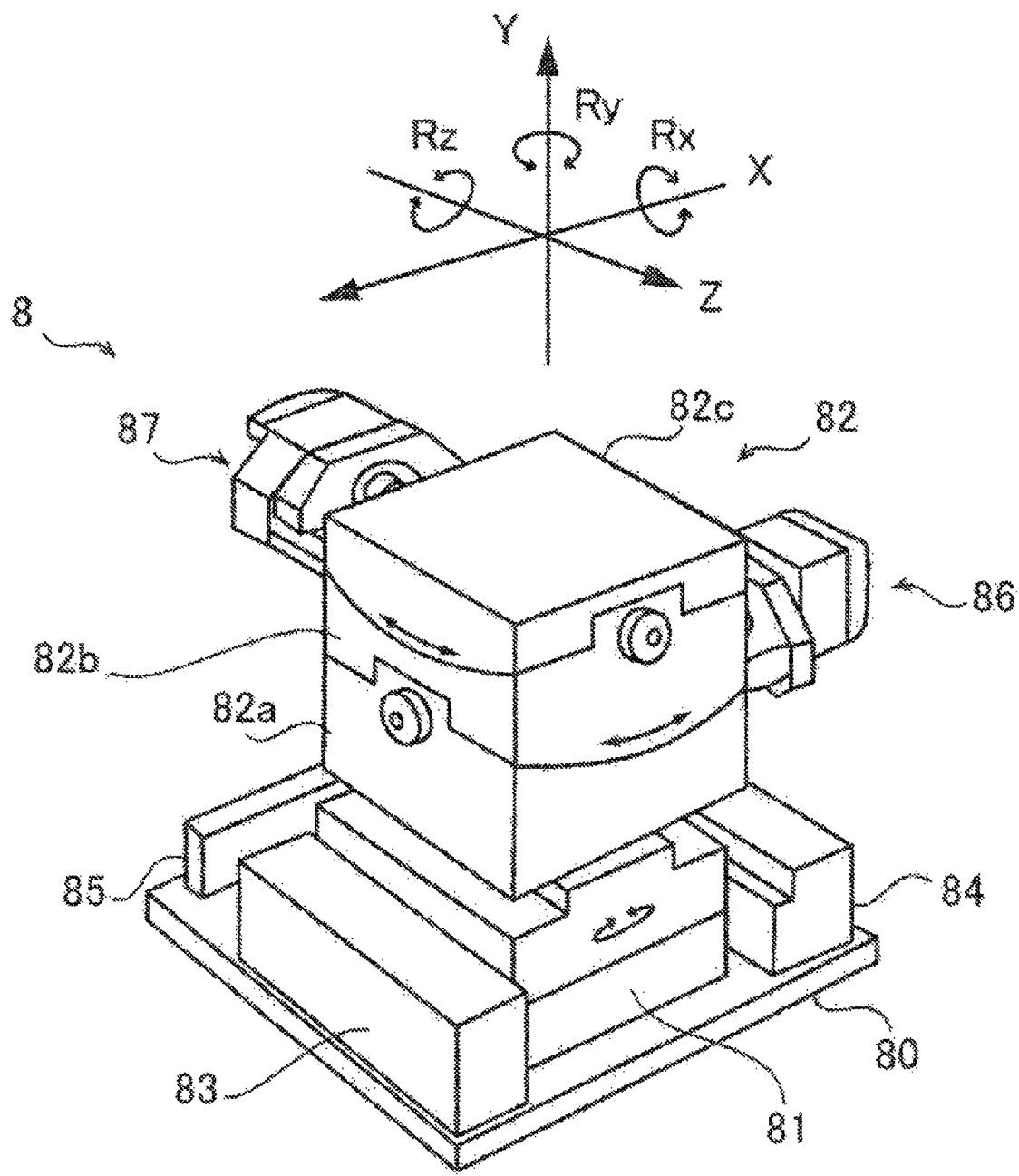
FIG. 4 is a diagram for explaining the configuration of the adjustment mechanism of the X-ray phase contrast imaging system according to the first embodiment of the present invention.

As shown in FIG. 4, the adjustment mechanism 8 includes a base 80, a stage support 81, a stage 82 for mounting a grating, a first drive unit 83, a second drive unit 84, a third drive unit 85, a fourth drive unit 86, and a fifth drive unit 87. The stage 82 is composed of a connecting portion 82a, an about Z-direction axis rotating unit 82b, and an about X-axis direction rotating unit 82c. The first to fifth drive units 83 to 87, the about Z-direction axis rotating unit 82b, and the about X-axis direction rotating unit 82c may each be embodied as motors (e.g., servo motors).

The first drive unit 83, the second drive unit 84, and the third drive unit 85 are each provided on the upper surface of the base 80. The first drive unit 83 is configured to reciprocate the stage support 81 in the Z-direction. Further, the second drive unit 84 is configured to rotate the stage support 81 about the Y-axis direction. Further, the third drive unit 85 is configured to reciprocate the stage support 81 in the X-direction. The stage support 81 is connected to the connecting portion 82a of the stage 82. As the stage support 81 moves, the stage 82 also moves.

Further, the fourth drive unit 86 is configured to reciprocate the about Z-direction axis rotating unit 82b in the X-direction. The about Z-direction axis rotating unit 82b is formed so that the bottom surface thereof is formed into a convex curved surface toward the connecting portion 82a, and is configured to rotate the stage 82 about the central axis of the Z-direction by being reciprocated in the X-direction. Further, the fifth drive unit 87 is configured to reciprocate the about X-axis direction rotating unit 82c in the Z-direction. The about X-axis direction rotating unit 82c is formed so that the bottom surface thereof is formed into a convex curved shape toward the about Z-direction axis rotating unit 82b, and is configured to rotate the stage 82 about the central axis of the X-direction by being reciprocated in the Z-direction.

Therefore, the adjustment mechanism 8 is configured so that the grating can be adjusted in Z-direction by the first drive unit 83. Further, the adjustment mechanism 8 is configured so that the grating can be adjusted in the rotational direction (Ry-direction) about the Y-axis direction by the second drive unit 84. Further, the adjustment mechanism 8 is configured so that the grating can be adjusted in the X-direction by the third drive unit 85. Further, the adjustment mechanism 8 is configured so that the grating can be adjusted in the rotational direction (Rz-direction) about the Z-direction axis by the fourth drive unit 86. Further, the adjustment mechanism 8 is configured so that the grating can be adjusted in the rotational direction (Rx-direction) about the X-axis direction by the fifth drive unit 87. The reciprocating movement in each axial direction is, for example, several millimeters. The rotatable angle in the rotational direction Rx about the X-axis direction, the rotational direction Ry about the Y-axis direction, and the rotational direction Rz about the Z-direction axis are each, for example, several degrees.

(Adjustment Method of Grating Positional Displacement)

Next, with reference to FIG. 5 to FIG. 16, a configuration in which the X-ray phase contrast imaging system 100 in the first embodiment adjusts the positional displacement of the first grating 3 or the second grating 4 will be described.

Figure 5:
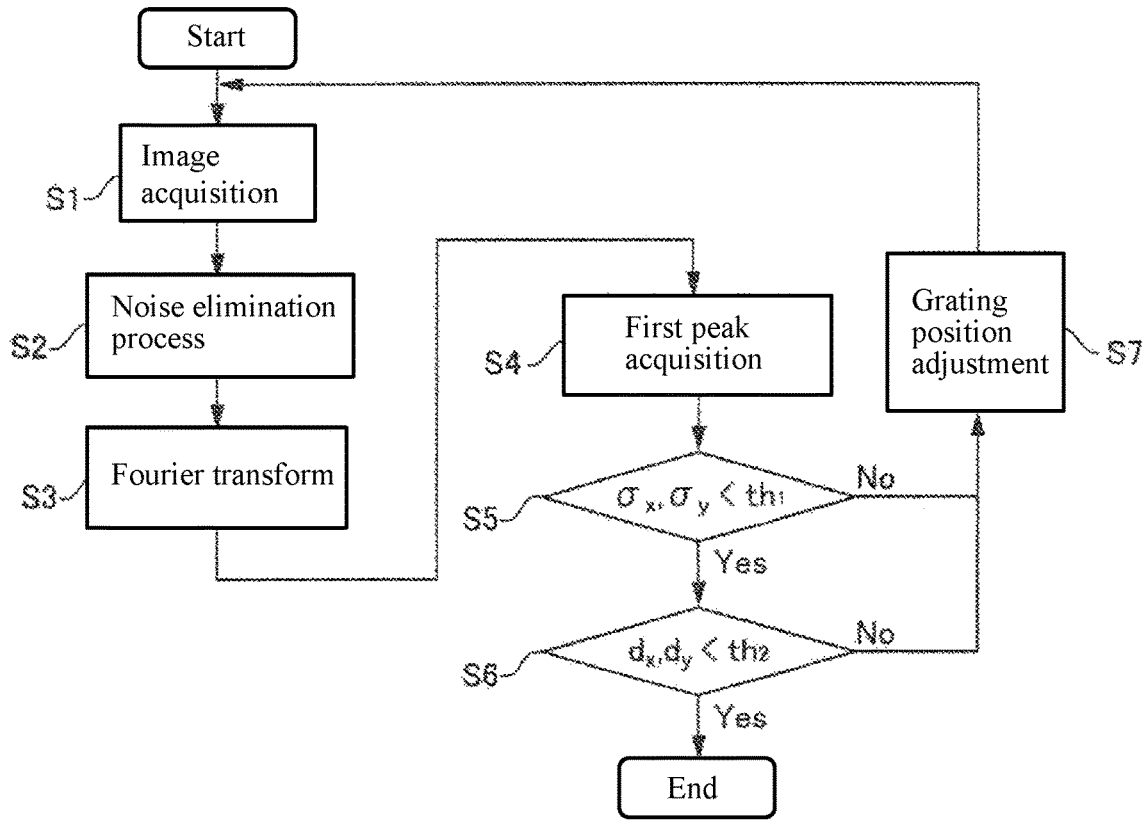
FIG. 5 is a flowchart for adjusting the positional displacement of the grating in the X-ray phase contrast imaging system according to the first embodiment of the present invention.

First, with reference to FIG. 5 and FIG. 6, the overall flow of the method of adjusting the grating by the X-ray phase contrast imaging system 100 in the first embodiment will be described.

In Step S1, the detector 5 acquires the self-image 30 of the first grating 3 and the image of the second grating 4. In Step S1, the image acquisition is performed without arranging the object T. Here, when the relative position between the first grating 3 and the second grating 4 is different from the designed position, an unintended moire fringe 12 (see FIG. 6A) is generated.

Next, in Step S2, the noise elimination processing section 11 eliminates the frequency component noise from the image acquired in Step S1. That is, the noise elimination processing section 11 performs filtering by a window function, a dark correction, a gain correction, and a defect correction.

Figure 10:
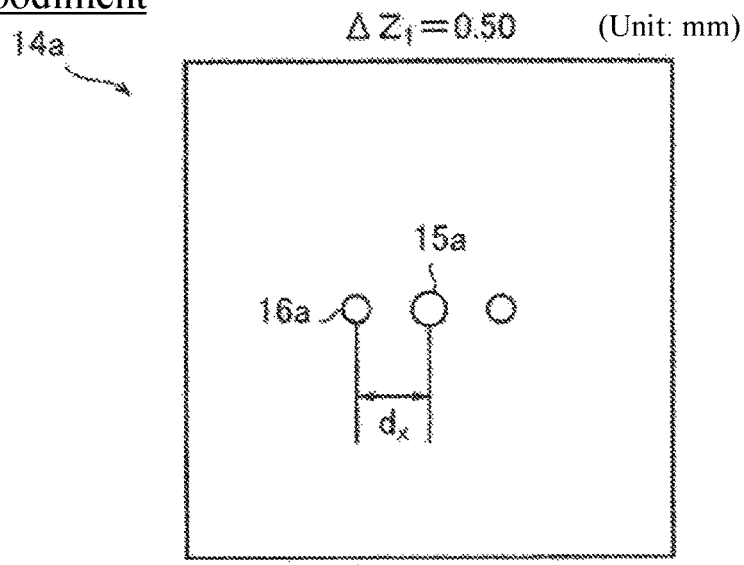
FIG. 10 is an enlarged view of a Fourier transform image when the first grating is displaced in the Z-direction.

Next, in Step S3, the control section 9 two-dimensionally Fourier transforms the image subjected to the noise illumination process in Step S2 to generate a Fourier transform image 14 (see FIG. 10).

Next, in Step S4, the image processing section 10 obtains the distance between the zero-order peak 15 (see FIG. 10) and the first-order peak 16 (see FIG. 10) and the magnitude of the first-order peak 16 in the Fourier transform image 14. Here, note that the zero-order peak 15 denotes a peak derived from the low frequency component in the image. Further, note that the first-order peak 16 denotes a peak derived from the frequency component of the unintended moire fringe 12 generated by the positional displacement between the self-image 30 of the first grating 3 and the second grating 4.

Next, in Step S5, the control section 9 obtains the positional displacement of the grating based on the magnitude of the first-order peak 16. When there is no positional displacement of the grating, the process proceeds to Step S6. When there is a positional displacement of the grating, the process proceeds to Step S7.

In Step S6, the control section 9 acquires the positional displacement of the grating based on the distance between the zero-order peak 15 and the first-order peak 16. When there is no positional displacement of the grating, the process ends here. When there is a positional displacement of the grating, the process proceeds to Step S7.

In Step S7, the control section 9 outputs a signal for correcting the positional displacement of the grating to the adjustment mechanism controller 7. Then, the adjustment mechanism controller 7 adjusts the positional displacement of the first grating 3 or the second grating 4 via the adjustment mechanism 8 based on the signal for correcting the positional displacement of the grating. Thereafter, the process proceeds to Step S1.

In the first embodiment, the X-ray phase contrast imaging system 100 is configured to adjust the positional displacement in the rotational direction Rx about the central axis of the X-direction and the positional displacement in the rotational direction Ry about the central axis of the Y-direction based on the positional displacement of the grating acquired by the grating positional displacement acquisition unit 6. After that, the X-ray phase contrast imaging system is configured to adjust the positional displacement in the rotational direction Rz about the Z-direction axis and the positional displacement in the Z-direction.

In the first embodiment, the X-ray phase contrast imaging system 100 is configured to repeatedly perform Step S1 to Step S7 until the positional displacement amount ($\sigma_x$, $\sigma_y$, and $d_x$, $d_y$) of the first grating 3 or the second grating 4 becomes equal to or less than the threshold value (th1 and th2).

Figure 6A:
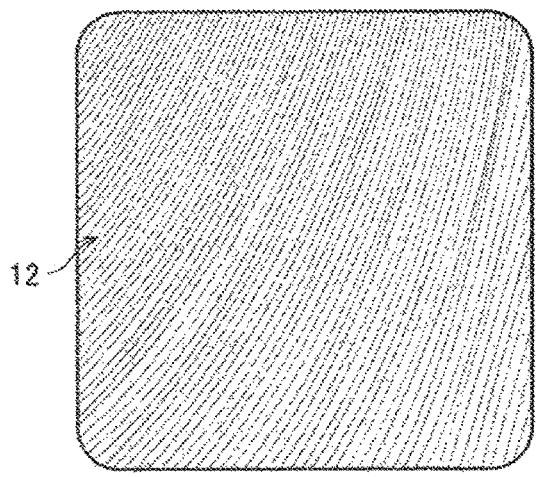
FIG. 6A is a diagram showing an image before the adjustment of the positional displacement of the grating.
Figure 6B:
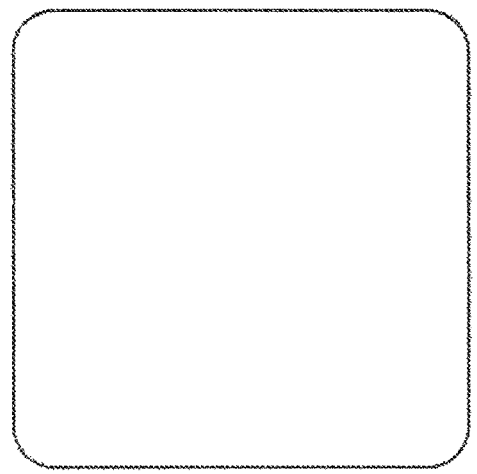
FIG. 6B is a diagram showing an image after the adjustment of the positional displacement of the grating.

FIG. 6A is a diagram showing an example of an image when there is a positional displacement of the grating. Further, FIG. 6B is a diagram showing an example after adjusting the positional displacement of the grating. Before adjusting the positional displacement of the grating, as shown in FIG. 6A, an unintended moire fringe 12 is generated in the acquired image by the self-image 30 of the first grating 3 and the second grating 4. In this case, by adjusting the positional displacement of the grating, the unintended moire fringe 12 is eliminated from the acquired image as shown in FIG. 6B.

(Acquisition of Positional Displacement of First Grating or Second Grating)

Next, with reference to FIG. 1, FIG. 3 and FIG. 7 to FIG. 16, a configuration for acquiring the positional displacement of the first grating 3 or the second grating 4 will be described.

<Acquisition of Positional Displacement in Z-Direction>

First, with reference to FIG. 1 and FIG. 7 to FIG. 10, the configuration in which the grating positional displacement acquisition unit 6 in the first embodiment acquires the positional displacement of the first grating 3 or the second grating 4 in the Z-direction will be described.

In the first embodiment, the grating positional displacement acquisition unit 6 is configured to acquire the positional displacement of the first grating 3 or the second grating 4 in the Z-direction based on the distance between the zero-order peak 15 and the first-order peak 16 in the Fourier transform image 14.

Here, as shown in FIG. 1, when the first grating 3 and the second grating 4 are arranged so that the distance between the first grating 3 and the second grating 4 in the Z-direction is a Talbot distance (ZT), the period $p_3$ of the self-image 30 of the first grating 3 becomes equal to the period $p_2$ of the second grating 4. Therefore, no unintended moire fringe is generated.

Figure 7:
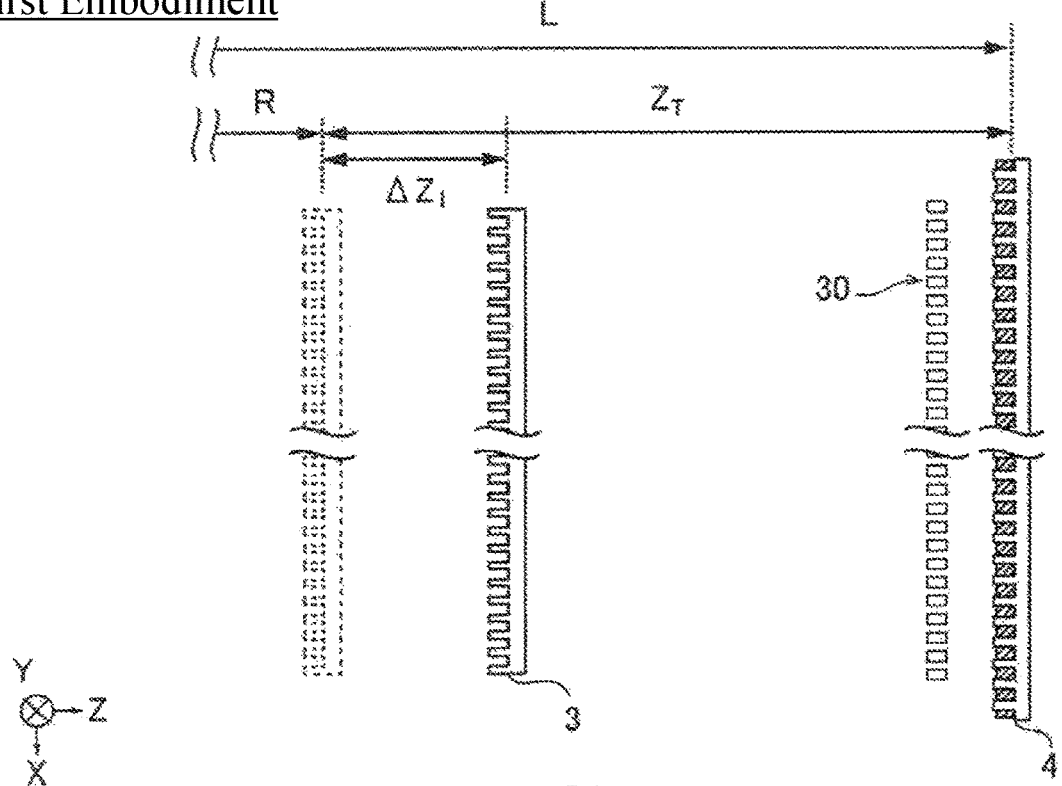
FIG. 7 is an enlarged view showing the state when the first grating is displaced in the Z-direction.
Figure 8:
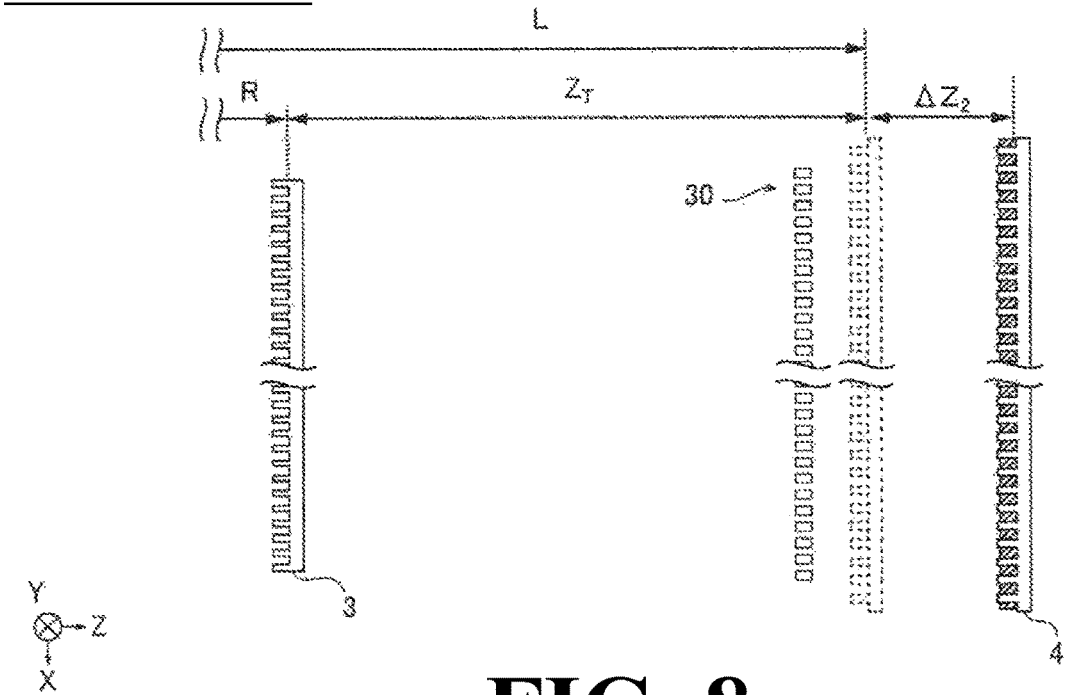
FIG. 8 is an enlarged view showing the state when the second grating is displaced in the Z-direction.

However, as shown in FIG. 7 and FIG. 8, when the distance between the first grating 3 and the second grating 4 in the Z-direction is deviated from the Talbot distance (ZT), the period $p_3$ of the self-image 30 of the first grating 3 changes. Therefore, the moire fringe 12a (see FIG. 9) is observed due to the periodic difference between the period $p_3$ of the self-image 30 of the first grating 3 and the period $p_2$ of the second grating 4.

Figure 9:
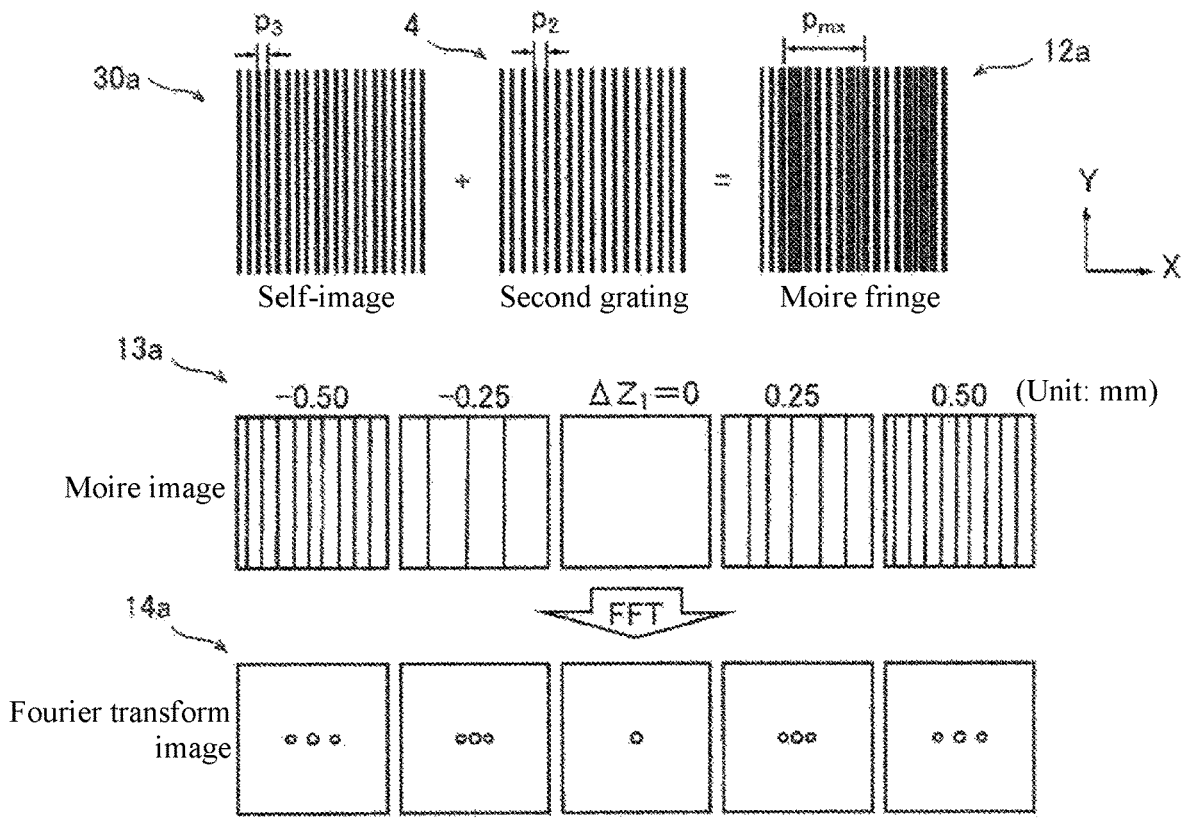
FIG. 9 is a diagram for explaining an unintended moire fringe and a Fourier transform image generated when the first grating is displaced in the Z-direction.

As shown in FIG. 9, when there is no positional displacement in the first grating 3 ($\Delta Z_1$ is 0), the period $p_3$ of the self-image 30a of the first grating 3 and the period $p_2$ of the second grating 4 are equal to each other, so no moire fringe 12a is formed in the acquired image. Also, when there is no positional displacement in the first grating 3 ($\Delta Z_1$ is 0), only the zero-order peak 15a is detected in the Fourier transform image 14a. Further, in the moire fringe image 13a, the period of the moire fringe 12a becomes smaller as the first grating 3 moves away (the absolute value of $\Delta Z_1$ increases) from the normal position (the position where the distance between the first grating 3 and the second grating 4 is the Talbot distance ZT). Further, in the Fourier transform image 14a, as the first grating 3 moves away from (the absolute value of $\Delta Z_1$ increases) the normal position (the position where the distance between the first grating 3 and the second grating 4 is the Talbot distance ZT), the distance dx between the zero-order peak 15a and the first-order peak 16a becomes large. The unit of the positional displacement amount $\Delta Z_1$ of the first grating 3 in FIG. 9 and FIG. 10 is "mm (millimeter)".

FIG. 10 is an example of an enlarged view of the Fourier transform image 14a in the case where the positional displacement amount $\Delta Z_1$ of the first grating 3 in the Z-direction is 0.50 mm. The "dx" is a distance between the zero-order peak 15a and the first-order peak 16a in the X-direction. In the first embodiment, the grating positional displacement acquisition unit 6 is configured to acquire the positional displacement of the first grating 3 or the second grating 4 in the Z-direction based on the distance dx between the zero-order peak 15a and the first-order peak 16a. Hereinafter, a detailed configuration in which the grating positional displacement acquisition unit 6 obtains the positional displacement of the first grating 3 or the second grating 4 will be described.

As shown in FIG. 6, when the first grating 3 is displaced by $\Delta Z_1$ in the Z-direction, the period $p_3$ of the self-image 30a of the first grating 3 is expressed by the following Equation (1).

$$p_3 = \frac{L}{R+\Delta Z_1} p_1 \tag{1}$$

At this time, on the detection surface of detector 5, the moire fringe 12a oscillating in the X-direction is observed by the periodic difference of the self-image 30a and the second grating 4. The period $p_{mx}$ of this moire fringe 12a is expressed by the following Equation (2).

$$p_{mx} = \frac{p_2 p_3}{|p_2 - p_3|} \tag{2}$$

On the other hand, when "dx" (the distance to the zero-order peak 15a) when the moire fringe image 13a is Fourier transformed is the position of the first-order peak 16a in the X-direction, the period $p_{mx}$ of the moire fringe 12a is expressed by the following Equation (3):

$$p_{mx} = \frac{N_x s_x}{d_x} \tag{3}$$

Here, the "Nx" is the number of pixels of the acquired image in the X-direction. Also, the "$s_x$" is the pixel size of the detector 5 in the X-direction.

When "$p_{mx}$" is eliminated from the aforementioned Equations (2) and (3), the following Equation (4) is obtained:

$$d_x = \frac{N_x s_x}{p_2 p_3} |p_2 - p_3| \tag{4}$$

Here, the period $p_2$ of the second grating 4 becomes equal to the period $p_3$ of the self-image 30a when there is no positional displacement ($\Delta Z_1=0$) and is expressed by the following Equation (5):

$$p_2 = \frac{L}{R} p_1 \tag{5}$$

By substituting the aforementioned Equations (1) and (5) into the aforementioned Equation (4), the following Equation (6) is obtained:

$$d_x = \frac{N_x s_x}{R p_2} |\Delta Z_1| \tag{6}$$

By modifying the aforementioned Equation (6), the following Equation (7) is obtained:

$$\Delta Z_1 = \pm \frac{R p_2 d_x}{N_x s_x} \tag{7}$$

As can be understood from the aforementioned Equation (7), the positional displacement amount $\Delta Z_1$ of the first grating 3 in the Z-direction can be calculated by measuring the "dx".

On the other hand, as shown in FIG. 8, when the second grating 4 is displaced by $\Delta Z_2$ in the Z-direction, the period $p_3$ of the self-image 30a of the first grating 3 is expressed by the following Equation (8):

$$p_3 = \frac{L+\Delta Z_2}{R} p_1 \tag{8}$$

Since the period $p_2$ of the second grating 4 is expressed by the aforementioned Equation (5), by substituting Equation (5) and Equation (8) into the Equation (4), the following Equation (9) is obtained:

$$d_x = \frac{N_x s_x}{p_2} \left| \frac{\Delta Z_2}{L+\Delta Z_2} \right| \tag{9}$$

By modifying Equation (9), the following Equation (10) is obtained:

$$\Delta Z_2 = \frac{\pm p_2 d_x L}{N_x s_x \mp p_2 d_x} \tag{10}$$

As can be understood from Equation (10), the positional displacement amount $\Delta Z_2$ of the second grating 4 in the Z-direction can be calculated by measuring the "dx" in the same manner as the positional displacement amount $\Delta Z_1$ of the first grating 3 in the Z-direction. Then, the control section 9 outputs the positional displacement amount $\Delta Z_1$ of the first grating 3 in the Z-direction or the positional displacement amount $\Delta Z_2$ of the second grating 4 in the Z-direction to the adjustment mechanism controller 7 as a signal for correcting the positional displacement.

<Acquisition of Positional Displacement in Rotational Direction About Z-Direction Axis>

Next, with reference to FIG. 3, FIG. 11 and FIG. 12, a configuration will be described in which the grating positional displacement acquisition unit 6 in the first embodiment acquires the positional displacement of the first grating 3 in the rotational direction Rz about the Z-direction axis. The unit of the positional displacement amount $\Delta Rz_1$ of the first grating 3 in the rotational direction Rz about the Z-direction axis in FIG. 11 and FIG. 12 is "degree".

In the first embodiment, the grating positional displacement acquisition unit 6 is configured to acquire the positional displacement of the first grating 3 or the second grating 4 in the rotational direction Rz about the Z-direction axis based on the Fourier transform image 14b. Note that the rotational direction Rz about the Z-direction axis is an example of the "rotational direction of the X-ray about the optical axis direction" recited in claims.

As shown in FIG. 3, in the case where the first grating 3 and the second grating 4 have no positional displacement in the rotational direction Rz about the Z-direction axis, the periodic direction of the self-image 30 of the first grating 3 matches the periodic direction of the second grating 4, so no unintended moire fringe 12 will be observed. However, when the first grating 3 is displaced by $\Delta Rz_1$, the self-image 30b is formed so as to be also inclined as shown in the example of FIG. 11, so the observed moire fringe 12b is formed in the Y-direction. Further, as the absolute value of $\Delta Rz_1$ increases, the period of the moire fringe 12b becomes smaller, and the distance $d_y$ in the Y-direction between the zero-order peak 15b and the first-order peak 16b of the obtained Fourier transform image 14b becomes larger.

Figure 11:
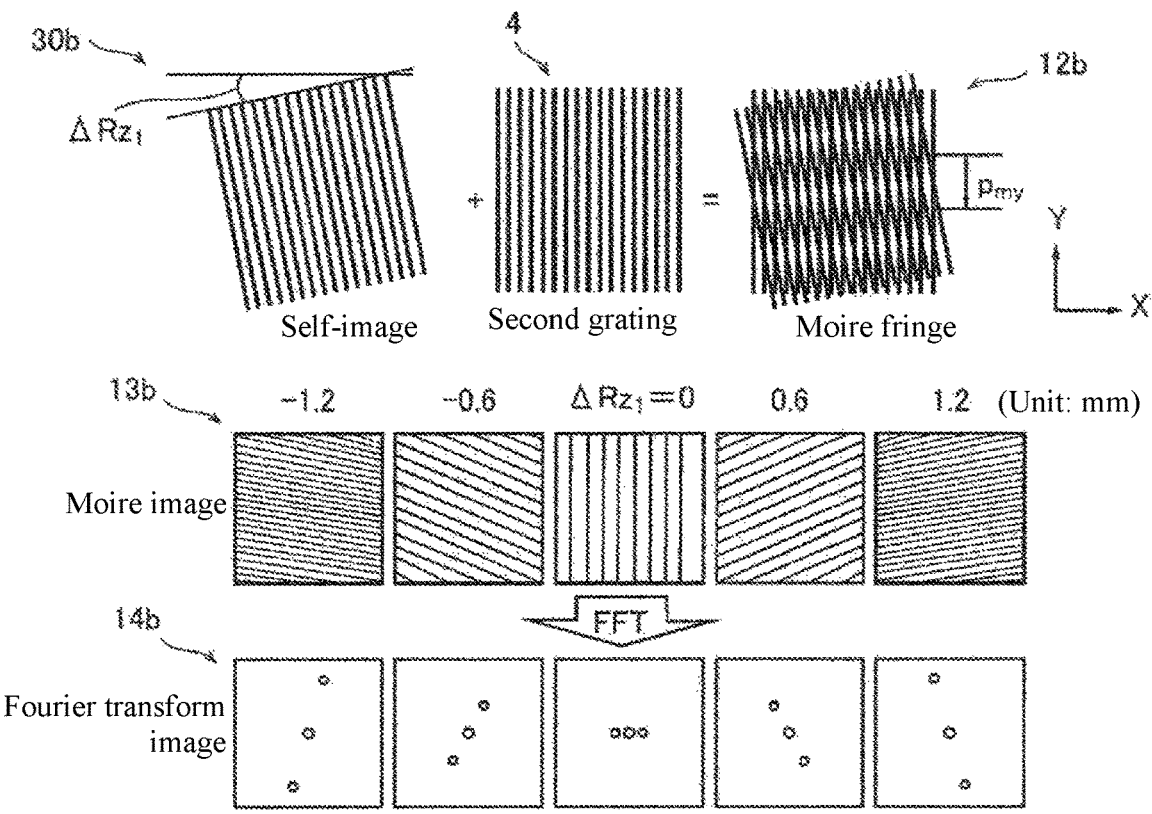
FIG. 11 is a diagram for explaining an unintended moire fringe and a Fourier transform image generated when the first grating is displaced in the rotational direction about the Z-direction axis.
Figure 12:
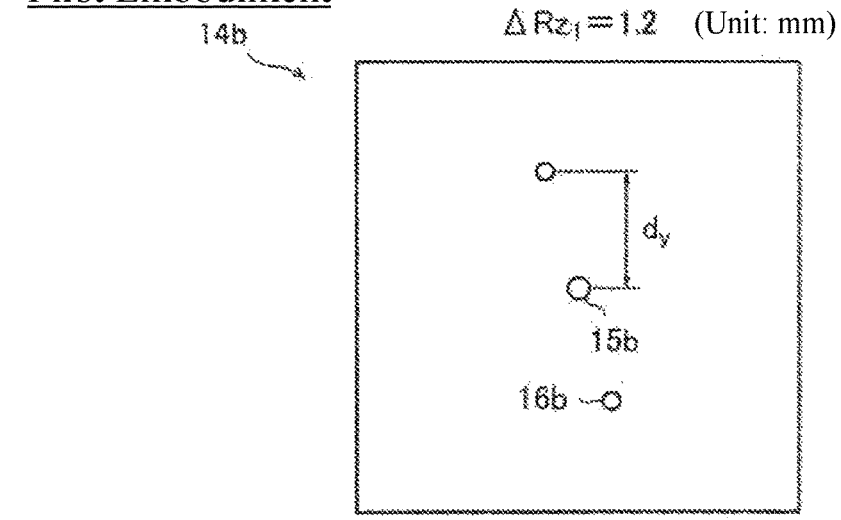
FIG. 12 is an enlarged view of the Fourier transform image when the first gratins is displaced in the rotational direction about the Z-direction axis.

FIG. 11 shows an example in which the positional displacement amount $\Delta Rz_1$ of the first grating 3 in the rotational direction Rz about the Z-direction axis is 1.2 degrees. Further, in FIG. 11, the reason why the first-order peak 16b is displaced in the X-direction is that it is configured to adjust the positional displacement of the first grating 3 and the second grating 4 in the rotational direction Rz about the Z-direction axis before adjusting the positional displacement of the first grating 3 and the second grating 4 in the Z-direction.

The period $p_{my}$ of the moire fringe 12b which is generated when the first grating 3 is displaced by $\Delta Rz_1$ in the rotational direction Rz about the Z-direction axis is represented by the following Equation (11) when $\Delta Rz_1$ is close to 0:

$$p_{my} = \frac{p_2}{|2\sin(\Delta Rz_1/2)|} \approx \frac{p_2}{|\Delta Rz_1|} \tag{11}$$

On the other hand, the position $d_y$ (distance to the zero-order peak 15b) of the first-order peak 16b of the Fourier transform image 14b in the Y-direction and the period $p_{my}$ of the moire fringe 12b have the relationship expressed by the following Equation (12):

$$p_{mx} = \frac{N_y s_y}{d_y} \tag{12}$$

Here, "Ny" is the pixel of the acquired image in the Y-direction pixel. Further, "$s_y$" is a pixel size of the detector 5 in the Y-direction.

By deleting "$p_{my}$" from Equation (11) and Equation (12), the following Equation (13) is obtained:

$$d_y = \frac{N_y s_y}{p_2} |\Delta Rz_1| \tag{13}$$

By modifying Equation (13), the following Equation (14) is obtained:

$$\Delta Rz_1 = \pm \frac{d_y p_2}{N_y s_y} \tag{14}$$

From the aforementioned Equation (14), it is understood that the positional displacement amount $\Delta Rz_1$ of the first grating 3 in the rotational direction Rz about the Z-direction axis is proportional to "$d_y$". Note that the unit of $\Delta Rz_1$ is "radian".

Further, the positional displacement amount $\Delta Rz_2$ in the case where the second grating 4 is displaced in the rotational direction Rz about the Z-direction axis is a relative rotational displacement between the first grating 3 and the second grating 4. Therefore, the positional displacement amount $\Delta Rz_2$ is equal to $\Delta Rz_1$, and is represented by the following Equation (15). Note that the unit of $\Delta Rz_2$ is "radian".

$$\Delta Rz_2 = \pm \frac{d_y p_2}{N_y s_y} \tag{15}$$

As can be understood from Equation (15), the positional displacement amount $\Delta Rz_2$ of the second grating 4 in the rotational direction Rz about the Z-direction axis is also proportional to "$d_y$". Therefore, the positional displacement of the first grating 3 and the second grating 4 in the rotational direction Rz about the Z-direction axis can be calculated by measuring "$d_y$". Then, the control section 9 outputs the positional displacement amount $\Delta Rz_1$ of the first grating 3 in the rotational direction Rz about the Z-direction axis or the positional displacement amount $\Delta Rz_2$ of the second grating 4 in the rotational direction Rz about the Z-direction axis to the adjustment mechanism controller 7 as a signal for correcting the positional displacement.

<Acquisition of Positional Displacement in Rotational Direction Rx About Central Axis of X-Direction>

Figure 13:
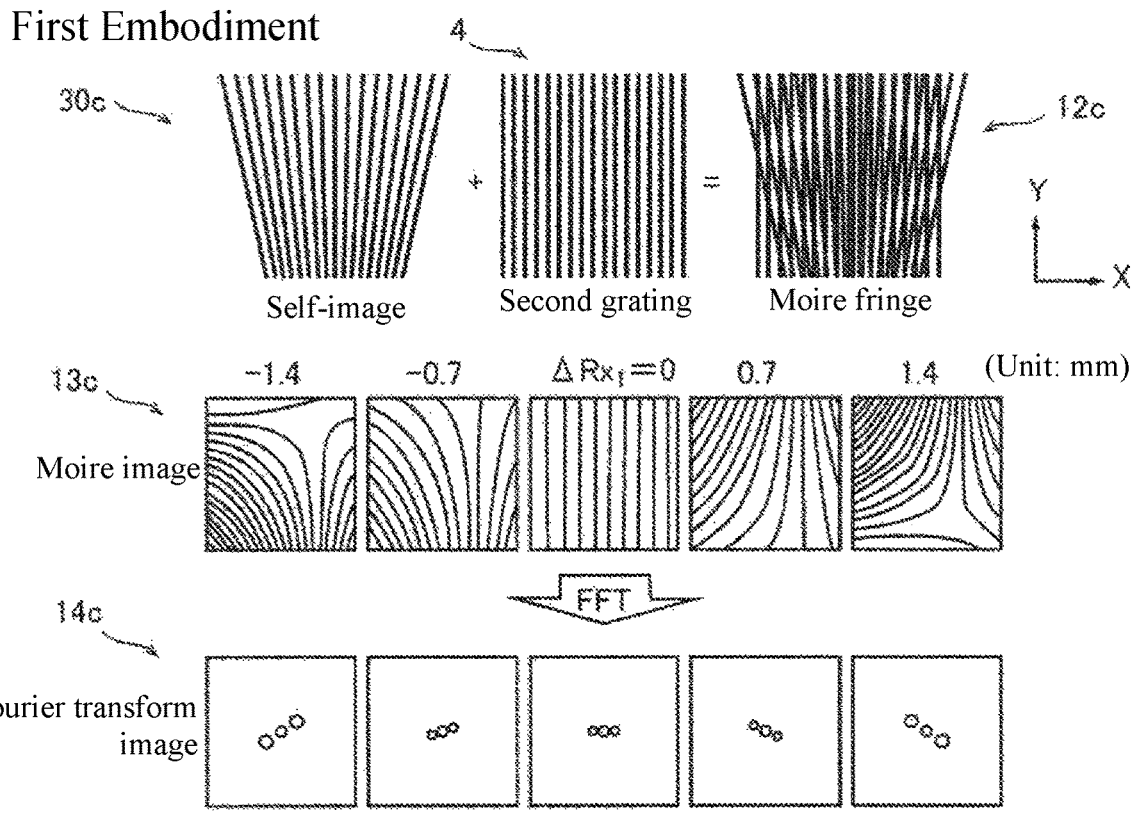
FIG. 13 is a diagram for explaining an unintended moire fringe and a Fourier transform image generated when the first grating is displaced in the rotational direction about the central axis of the X-direction.
Figure 14:
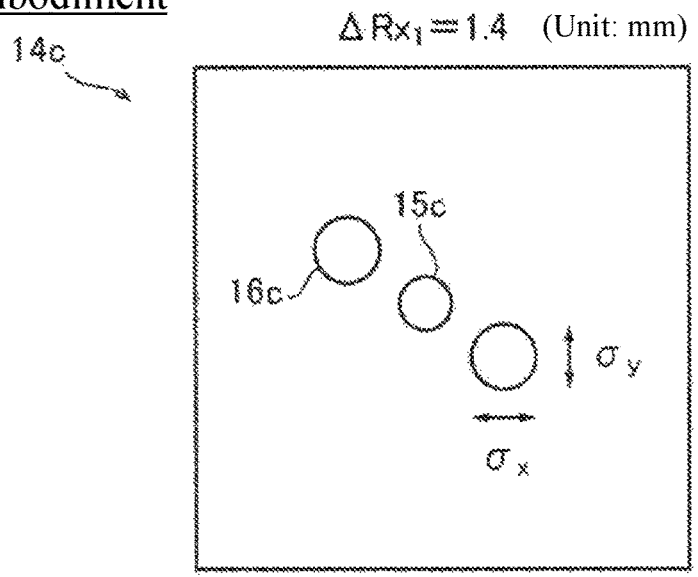
FIG. 14 is an enlarged view of a Fourier transform image when the first gratins is displaced in the rotational direction about the central axis of the X-direction.

Next, with reference to FIG. 3, FIG. 13 and FIG. 14, a configuration will be described in which the grating positional displacement acquisition unit 6 in the first embodiment acquires the positional displacement in the rotational direction Rx about the central axis of the X-direction. The unit of the positional displacement amount $\Delta Rx_1$ of the first grating 3 in the rotational direction Rx about the central axis of the X-direction in FIG. 13 and FIG. 14 is "degrees".

In the first embodiment, the grating positional displacement acquisition unit 6 is configured to acquire the positional displacement of the first grating 3 or the second grating 4 in the rotational direction Rx about the central axis of the X-direction of the first grating 3 or the second grating 4 based on the magnitude of the first-order peak 16c in the Fourier transform image 14c.

As shown in FIG. 3, in the case where the first grating 3 and the second grating 4 have no positional displacement in the rotational direction Rx about the central axis of the X-direction, the frequency of the self-image 30 of the first grating 3 in the detection surface matches the frequency of the second grating 4. Therefore, no unintended moire fringe 12 will be observed. However, in the case where the first grating 3 is displaced in the rotational direction Rx about the central axis of the X-direction, the magnification ratio of the first grating 3 changes, so the self-images 30c which are different in frequency above and below the detection surface are formed. At this time, the moire fringe 12c as shown in the example of FIG. 13 is generated. As the positional displacement amount $\Delta Rx_1$ of the first grating 3 in the rotational direction Rx about the central axis of the X-direction increases, the distortion of the generated moire fringe 12c also increases.

In the case where the first grating 3 is displaced in the rotational direction Rx about the central axis of the X-direction, the moire fringe 12c to be observed becomes a shape distorted in the upward, downward, leftward and rightward directions, and has an intensity distribution containing a plurality of frequency components in the X-direction and the Y-direction. Therefore, as shown in the example of FIG. 14, the first-order peak 16c of the Fourier transform image 14c spreads in the X-direction and the Y-direction. Further, as the absolute value of $\Delta Rx_1$ increases, the spread of the first-order peak 16c in the X-direction and the Y-direction increases. Therefore, the positional displacement amount $\Delta Rx_1$ of the first grating 3 in the rotational direction Rx about the central axis of the X-direction, the magnitude $\sigma_x$ of the first-order peak 16c in the X-direction, and the magnitude $\sigma_y$ of the first-order peak 16c in the Y-direction are correlated.

In this way, acquisition of the positional displacement based on the magnitude of the first-order peak 16 can be paraphrased as acquisition of the positional displacement of the grating based on the magnitude of the dispersion of the frequency component constituting the first-order peak 16.

Further, also in the case where the second grating 4 is displaced in the rotational direction Rx about the central axis of the X-direction, the relative rotational displacement between the first grating 3 and the second grating 4 is the same as when the first grating 3 is displaced. Therefore, in the same manner as $\Delta Rx_1$, the displacement amount $\Delta Rx_2$ in the case where the second grating 4 is displaced in the rotational direction Rx about the central axis of the X-direction is correlated with the magnitude $\sigma_x$ of the first-order peak 16c in the X-direction and the magnitude $\sigma_y$ of the first-order peak 16c in the Y-direction.

FIG. 14 shows an example in which the positional displacement amount $\Delta Rx_1$ of the first grating 3 in the rotational direction Rx about the central axis of the X-direction is 1.4 degrees. In FIG. 13, the reason why the first-order peak 16c is displaced in the X-direction is that it is configured that the positional displacements of the first grating 3 and the second grating 4 in the rotational direction Rx about the central axis of the X-direction are adjusted before adjusting the positional displacements of the first grating 3 and the second grating 4 in the Z-direction.

<Acquisition of Positional Displacement in Rotational Direction Ry About Central Axis of Y-Axis Direction>

Figure 15:
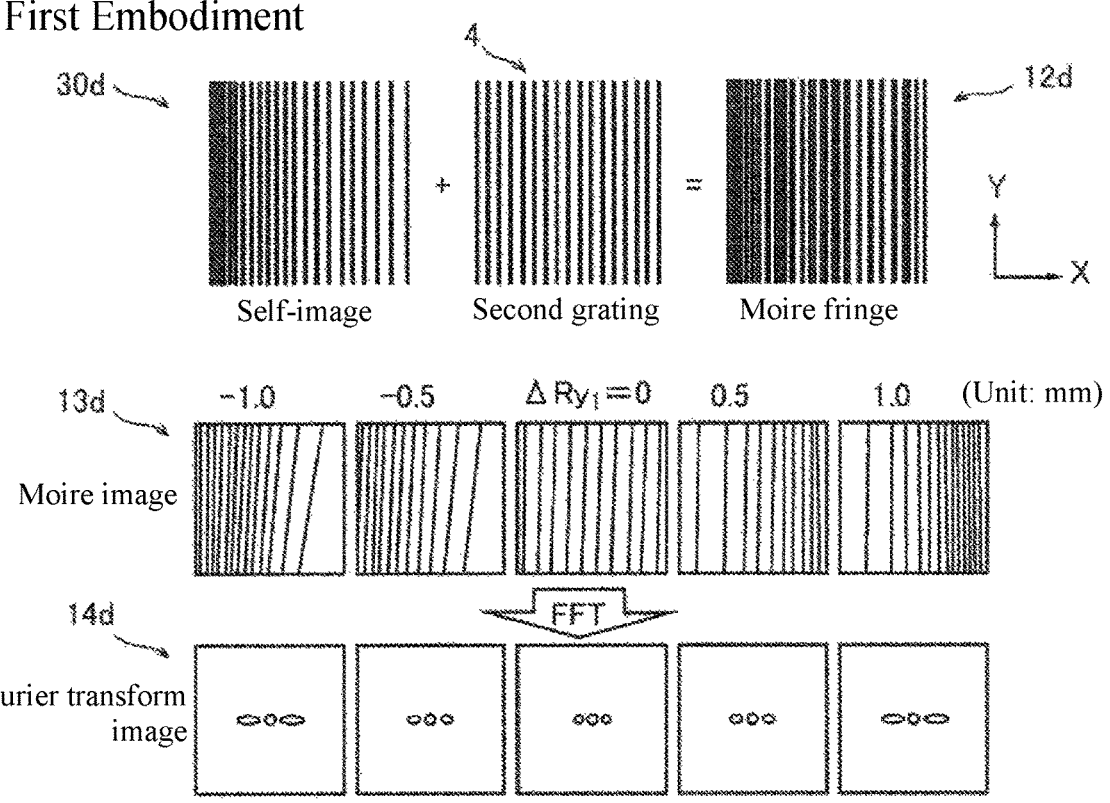
FIG. 15 is a diagram for explaining an unintended moire fringe and a Fourier transform image generated when the first grating is displaced in the rotational direction about the central axis of the Y-direction.
Figure 16:
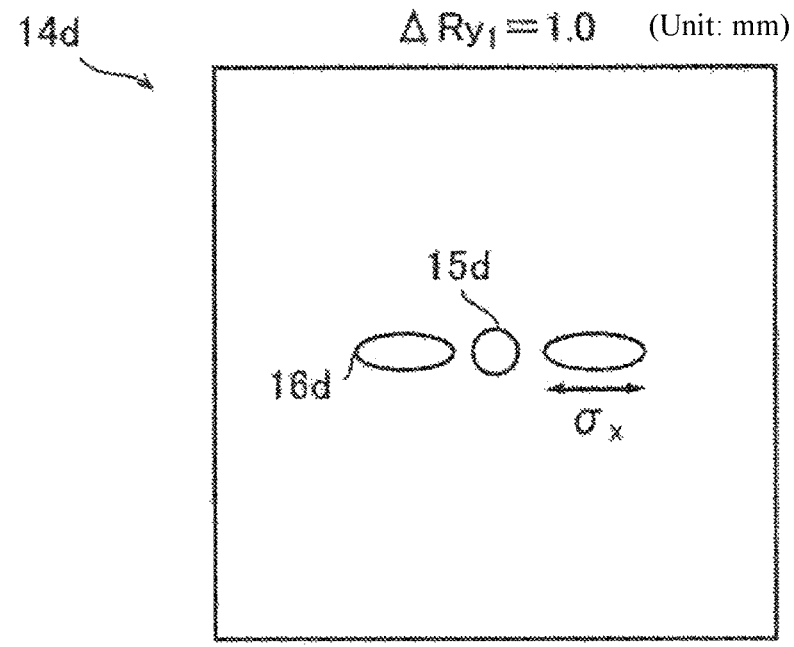
FIG. 16 is an enlarged view of a Fourier transform image when the first grating is displaced in the rotational direction about the central axis of the Y-direction.

Next, with reference to FIG. 3, FIG. 15 and FIG. 16, a configuration will be described in which the grating positional displacement acquisition unit 6 in the first embodiment acquires the positional displacement in the rotational direction Ry about the central axis of the Y-direction. In FIG. 15 and FIG. 16, the unit of the positional displacement amount $\Delta Ry_1$ of the first grating 3 in the rotational direction Ry about the central axis of the Y-direction is "degree".

In the first embodiment, the grating positional displacement acquisition unit 6 is configured to acquire the positional displacement of the first grating 3 or the second grating 4 in the rotational direction Ry about the central axis of the Y-direction of the first grating 3 or the second grating 4 based on the magnitude of the first-order peak 16d in the Fourier transform image 14d.

As shown in FIG. 3, in the case where the first grating 3 and the second grating 4 have no positional displacement in the rotational direction Ry about the central axis of the Y-direction, the frequency of the self-image 30 of the first grating 3 on the detection surface matches the frequency of the second grating 4. Therefore, no unintended moire fringe 12 will be observed. However, in the case where the position of the first grating 3 in the rotational direction Ry about the central axis of the Y-direction is displaced, the magnification ratio of the first grating 3 changes, so the self-images 30d which are different in frequency above and below the detection surface are formed.

The moire fringe 12d generated by the interference between the self-image 30d and the second grating 4 becomes a shape distorted in the left and right, and becomes an intensity distribution including a plurality of frequency components in the X-direction. Therefore, when the position of the first grating 3 in the rotational direction Ry about the central axis of the Y-direction is displaced, as shown in FIG. 16, the first-order peak 16d of the Fourier transform image 14d spreads in the X-direction. As the absolute value of $\Delta Ry_1$ increases, the spread of the first-order peak 16d in the X-direction increases. That is, the positional displacement amount $\Delta Ry_1$ of the first grating 3 in the rotational direction Ry about the central axis of the Y-direction is correlated with the magnitude $\sigma_x$ of the first-order peak 16d of the Fourier transform image 14d in the X-direction.

Further, also in the case where the second grating 4 is displaced in the rotational direction Ry about the central axis of the Y-direction, the relative rotational displacement between the first grating 3 and the second grating 4 is the same as when the first grating 3 is displaced. Therefore, in the same manner as $\Delta Ry_1$, the displacement amount $\lambda Ry_2$ in the case where the second grating 4 is displaced in the rotational direction Ry about the central axis of the Y-direction is correlated with the magnitude $\sigma_x$ of the first-order peak 16d in the X-direction.

FIG. 16 shows an example in which the positional displacement amount $\Delta Ry_1$ of the first grating 3 in the rotational direction Ry about the central axis of the Y-direction is 1.0 degrees. Further, in FIG. 15 and FIG. 16, the reason why the first-order peak 16d is displaced in the X-direction is that it is configured that the positional displacements of the first grating 3 and the second grating 4 in the rotational direction Ry about the central axis of the Y-direction have been adjusted before adjusting the positional displacement of the first grating 3 and the second grating 4 in the Z-direction.

The positional displacement of the Z-direction, the positional displacement in the rotational direction Rz about the Z-direction axis, the positional displacement in the rotational direction Rx about the central axis of the X-direction, the positional displacement in the rotational direction Ry about the central axis of the Y-direction, the distance $(d_y, d_y)$ between the zero-order peak 15 and the first-order peak 16 in the Fourier transform image 14, and the magnitude $(\sigma_x, \sigma_y)$ of the first-order peak 16 in the Fourier transform image 14 have a relationship represented by the following Equation (16) to Equation (19).

$$\Delta Z_1, \Delta Z_2 \propto d_x \tag{16}$$

$$\Delta Rx_1, \Delta Rx_2 \propto \sigma_x, \sigma_y \tag{17}$$

$$\Delta Ry_1, \Delta Ry_2 \propto \sigma_x \tag{18}$$

$$\Delta Rz_1, \Delta Rz_2 \propto d_y \tag{19}$$

In the first embodiment, as described above, the grating positional displacement acquisition unit 6 is configured to acquire the magnitude of the positional displacement of the grating based on the distance ($d_y$, $d_y$) between the zero-order peak 15 and the first-order peak 16 in the Fourier transform image 14. Further, the grating positional displacement acquisition unit 6 is configured to obtain the presence or absence of the positional displacement of the grating based on the magnitude ($\sigma_x$, $\sigma_y$) of the first-order peak 16 in the Fourier transform image 14.

Here, in the first embodiment, the grating positional displacement acquisition unit 6 can acquire the positional displacement amount $\Delta Z$ of the grating in the Z-direction and the positional displacement amount $\Delta Rz$ in the rotational direction Rz about the Z-direction axis based on the distance ($d_y$, $d_y$) between the peaks of the Fourier transform image 14. However, in the first embodiment, the grating positional displacement acquisition unit 6 cannot directly calculate the positional displacement amount in the rotational direction Rx about the central axis of the X-direction and the positional displacement amount in the rotational direction Ry around the central axis of the Y-direction.

Therefore, in the first embodiment, the grating positional displacement acquisition unit 6 is configured to acquire a rotational amount that the magnitude ($\sigma_x$, $\sigma_y$) of the first-order peak 16 in the Fourier transform image 14 becomes the minimum value or near the minimum value as a positional displacement amount based on a plurality of Fourier transform images 14 captured by rotating either one of the first grating 3 and the second grating 4 in one direction.

Note that the rotation amount that the magnitude ($\sigma_x$, $\sigma_y$) of the first-order peak 16 becomes near the minimum value denotes a rotation amount in the range that the magnitude ($\sigma_x$, $\sigma_y$) of the first-order peak 16 in the Fourier transform image 14 captured a plurality of times by rotating either one of the first grating 3 and the second grating 4 in one direction becomes equal to or less than the predetermined threshold value th1.

The grating positional displacement acquisition unit 6 outputs the positional displacement amount $\Delta Z$ of the grating in the Z-direction to the adjustment mechanism controller 7 as the positional displacement amount of the grating. The grating positional displacement acquisition unit 6 outputs the positional displacement amount $\Delta Rz$ in the rotational direction Rz about the Z-direction axis as the positional displacement amount of the grating to the adjustment mechanism controller 7. Further, the grating positional displacement acquisition unit 6 outputs the rotational amount of the first grating 3 or the second grating 4 that the positional displacement amount in the rotational direction Rx about the central axis of the X-direction (the magnitude ($\sigma_x$, $\sigma_y$) of the first-order peak 16 in the Fourier transform image 14) becomes the minimum value or near the minimum value equal to or less than a predetermined threshold value th1 as the positional displacement amount of the grating to the adjustment mechanism controller 7. Further, the grating positional displacement acquisition unit 6 outputs the rotational amount of the first grating 3 or the second grating 4 that the positional displacement amount in the rotational direction Ry about the central axis of the Y-direction (the magnitude ($\sigma_x$) of the first-order peak 16 in the Fourier transform image 14) becomes the minimum value or near the minimum value equal to or less than a predetermined threshold value th1 as the positional displacement amount of the grating to the adjustment mechanism controller 7.

In the first embodiment, the X-ray phase contrast imaging system 100 is configured to adjust the positional displacement of the grating until the positional displacement of the first grating 3 or the second grating 4 becomes equal to or less than a predetermined threshold value (th1, th2). That is, the X-ray phase contrast imaging system 100 is configured to adjust the grating until the positional displacement amount (magnitude ($\sigma_x$, $\sigma_y$)) of the first-order peak 16 in the Fourier transform image 14) in the rotational direction Rx about the central axis of the X-direction becomes equal to or less than a predetermined threshold value th1.

Further, the X-ray phase contrast imaging system 100 is configured to adjust the grating until the positional displacement amount (magnitude ($\sigma_x$) of the first-order peak 16 in the Fourier transform image 14) in the rotational direction Ry about the central axis of the Y-direction becomes equal to or less than a predetermined threshold value th1.

Further, the X-ray phase contrast imaging system 100 is configured to adjust the grating so that the positional displacement amount $\Delta Z$ of the grating in the Z-direction becomes equal to or less than a predetermined threshold value th2. Further, it is configured to adjust the grating so that the positional displacement amount $\Delta Rz$ in the rotational direction Rz about the Z-direction axis becomes equal to or less than a predetermined threshold value th2.

In the first embodiment, the positional displacement amount $\Delta Z$ of the grating in the Z-direction and the positional displacement amount $\Delta Rz$ in the rotational direction Rz about the Z-direction axis can be directly calculated. Therefore, the X-ray phase contrast imaging system 100 is configured to adjust the grating to a position where the predetermined threshold value th2 becomes approximately 0.

Effects of First Embodiment

In the first embodiment, the following effects can be obtained.

In the first embodiment, as described above, the X-ray phase contrast imaging system 100 includes an X-ray source 1, a detector 5 for detecting an X-ray irradiated from the X-ray source 1, a plurality of gratings arranged between the X-ray source 1 and the detector 5 and including the first grating 3 for forming the self-image 30 of the first grating 3 by being irradiated by the X-ray from the X-ray source 1 and a second grating 4 for forming an interference fringe 12 with the self-image 30 of the first grating 3 by being irradiated by the X-ray that has passed through the first grating 3, and a grating positional displacement acquisition unit 6 for acquiring the positional displacement of the grating based on the Fourier transform image 14 acquired by Fourier transforming the interference fringe image 13 detected by the detector 5.

Here, when the relative position of the first grating 3 and the second grating 4 deviates from the design position, an unintended moire fringe 12 is generated. Therefore, in the Fourier transform image 14, in addition to the peak (zero-order peak 15) due to the self-image 30 of the first grating 3, a peak (first order peak 16) due to the unintended moire fringe 12 is generated. With this, the grating positional displacement acquisition unit 6 acquires the positional displacement of the grating based on Fourier transform image 14, the position adjustment of the grating can be performed based on the obtained positional displacement of the grating. Therefore, it is possible to adjust the positional displacement of the grating without depending on knowledge and/or experience of a measurer and to shorten the adjustment time.

Further, in the first embodiment, as described above, the X-ray phase contrast imaging system 100 further includes an adjustment mechanism 8 for adjusting the positional displacement of at least either one of the first grating 3 and the second grating 4, and is configured to correct the positional displacement of the grating based on the positional displacement of the grating acquired by the grating positional displacement acquisition unit 6.

With this configuration, it becomes possible to automatically correct the positional displacement of the grating by the adjustment mechanism 8 based on the positional displacement of the grating acquired by the grating positional displacement acquisition unit 6. Therefore, the positional displacement of the grating can be more easily adjusted without depending on knowledge and/or experience of a measurer. Further, the positional displacement of the grating by the adjustment mechanism 8 can be adjusted, so the adjustment time can be further shortened.

Further, in the first embodiment, as described above, the grating positional displacement acquisition unit 6 is configured to acquire the positional displacement of the grating based on at least one of the peak-to-peak distance ($d_x$, $d_y$) and the magnitude ($\sigma_x$, $\sigma_y$) of the peaks of the Fourier transform image 14. With this, the positional displacement of the grating can be acquired by the image processing of the Fourier transform image 14. As a result, the positional displacement of the grating can be automatically acquired without confirming the moire fringe 12 by the measurer's visual inspection.

Further, in the first embodiment, as described above, the grating positional displacement acquisition unit 6 is configured to acquire the positional displacement of the first grating 3 or the second grating 4 in the Z-direction based on the distance (dx) between the zero-order peak 15 and the first-order peak 16 in the Fourier transform image 14.

With this, the positional displacement of the first grating 3 or the second grating 4 in the Z-direction can be grasped by replacing the positional displacement with the magnitude of the distance (dx) between the zero-order peak 15 and the first-order peak 16 of the Fourier transform image 14. As a result, by adjusting the position of the grating so that the distance (dx) between the zero-order peak 15 and the first-order peak 16 of the Fourier transform image 14 becomes small, the positional displacement of the first grating 3 or the second grating 4 in the Z-direction can be easily adjusted.

Further, in the first embodiment, as described above, the grating positional displacement acquisition unit 6 is configured to acquire the positional displacement of the first grating 3 or the second grating 4 in the rotational direction Rz about the Z-direction axis based on the distance ($d_y$) between the zero-order peak 15 and the first-order peak 16 in the Fourier transform image 14.

With this, the positional displacement of the first grating 3 or the second grating 4 in the rotational direction Rz about the Z-direction axis can be grasped by replacing the positional displacement with the magnitude of the distance ($d_y$) between the zero-order peak 15 and the first-order peak 16 of the Fourier transform image 14. As a result, by adjusting the position of the grating so that the distance ($d_y$) between the zero-order peak 15 and the first-order peak 16 of the Fourier transform image 14 becomes small, the positional displacement of the first grating 3 or the second grating 4 in the rotational direction Rz about the Z-direction axis can be easily adjusted.

In the first embodiment, as described above, the grating positional displacement acquisition unit 6 is configured to acquire the magnitude of the positional displacement of the grating based on the distance ($d_y$, $d_y$) between the zero-order peak 15 and the first-order peak 16 in the Fourier transform image 14.

With this, the magnitude of the positional displacement of the grating can be acquired. As a result, by adjusting the position of the grating with the magnitude of the acquired positional displacement as a correction amount, the positional displacement of the first grating 3 or the second grating 4 can be more easily and accurately adjusted.

Further, in the first embodiment, as described above, the grating positional displacement acquisition unit 6 is configured to acquire the positional displacement of the first grating 3 or the second grating 4 in the rotational direction Ry about the central axis of the Y-direction of the first grating 3 or the second grating 4 based on the magnitude ($\sigma_x$) of the first-order peak 16 in the Fourier transform image 14.

With this, the positional displacement of the first grating 3 or the second grating 4 in the rotational direction Ry about the central axis of the Y-direction of the first grating 3 or the second grating 4 can be grasped by replacing the positional displacement with the magnitude ($\sigma_x$) of the first-order peak 16 of the Fourier transform image 14. As a result, by adjusting the grating so that the magnitude ($\sigma_x$) of the first-order peak 16 of the Fourier transform image 14 becomes small, the positional deviation of the first grating 3 or the second grating 4 in the rotational direction Ry about the central axis of the Y-direction of the first grating 3 or the second grating 4 can be easily adjusted.

Further, in the first embodiment, as described above, the grating positional displacement acquisition unit 6 is configured to acquire the positional displacement of the first grating 3 or the second grating 4 in the rotational direction Rx about the central axis of the X-direction of the first grating 3 or the second grating 4 based on the magnitude ($\sigma_x$, $\sigma_y$) of the first-order peak 16 in the Fourier transform image 14.

With this, the positional displacement of the first grating 3 or the second grating 4 in the rotational direction Rx about the central axis of the X-direction can be grasped by replacing the positional displacement with the magnitude ($\sigma_x$, $\sigma_y$) of the first-order peak 16 of the Fourier transform image 14. As a result, by adjusting the grating so that the magnitude ($\sigma_x$, $\sigma_y$) of the first-order peak 16 of the Fourier transform image 14 becomes small, the positional displacement of the first grating 3 or the second grating 4 in the rotational direction Rx about the central axis of the X-direction of the first grating 3 or the second grating 4 can be easily adjusted.

Further, in the first embodiment, as described above, the grating positional displacement acquisition unit 6 is configured to acquire the presence or absence of the positional displacement of the grating based on the magnitude ($\sigma_x$, $\sigma_y$) of the first-order peak 16 in the Fourier transform image 14.

With this configuration, it is possible to automatically judge the presence or absence of the positional displacement of the first grating 3 or the second grating 4 by the image processing of the Fourier transform image 14.

Further, in the first embodiment, as described above, the grating positional displacement acquisition unit 6 is configured to acquire the rotation amount that the magnitude ($\sigma_x$, $\sigma_y$) of the first-order peak 16 in the Fourier transform image 14 becomes the minimum value or near the minimum value as a positional displacement amount based on a plurality of Fourier transform images 14 captured by rotating either one of the first grating 3 and the second grating 4.

With this, the relative position of the grating where the positional displacement of the grating becomes as small as possible can be acquired based on a plurality of Fourier transform images 14. As a result, the positional displacement of the first grating 3 or the second grating 4 can be easily and accurately adjusted.

Further, in the first embodiment, as described above, the plurality of gratings further includes a third grating 2 arranged between the X-ray source 1 and the first grating 3.

With this, the coherence of the X-ray source 1 can be enhanced using the third grating 2. As a result, the X-ray phase contrast image capturing can be performed using the X-ray source 1 whose focal length is not minute, so that the freedom of selection of the X-ray source 1 can be enhanced.

Further, in the first embodiment, as described above, the X-ray phase contrast imaging system 100 further includes a noise elimination processing section 11 for eliminating the frequency noise from the image detected by the detector 5 before performing Fourier transform.

With this, it is possible to eliminate the artifact (virtual image) by the analysis of a finite space at the time of performing the Fourier transform and the artifact (virtual image) derived from the detector 5 before performing the Fourier transform. As a result, it is possible more accurately to detect the peak (first-order peak 16) due to the positional displacement of the grating obtained by the Fourier transform.

Second Embodiment

Next, with reference to FIG. 1, FIG. 2, FIG. 17 to FIG. 20, the X-ray phase contrast imaging system 200 (see FIG. 1) according to a first embodiment of the present invention will be described. Unlike the first embodiment in which the frequency noise is eliminated before performing the Fourier transform on the interference fringe image 13, in the second embodiment, the image processing section 10 (see FIG. 2) is configured to eliminate the noise 22 (see FIG. 18) generated in the Fourier transform image 14 using the Fourier transform reference image 23 (see FIG. 19) previously obtained by Fourier transforming the interference fringe image 13.

Note that the same reference numerals are allotted to the same configurations as those of the first embodiment, and the description thereof will be omitted.

Figure 17:
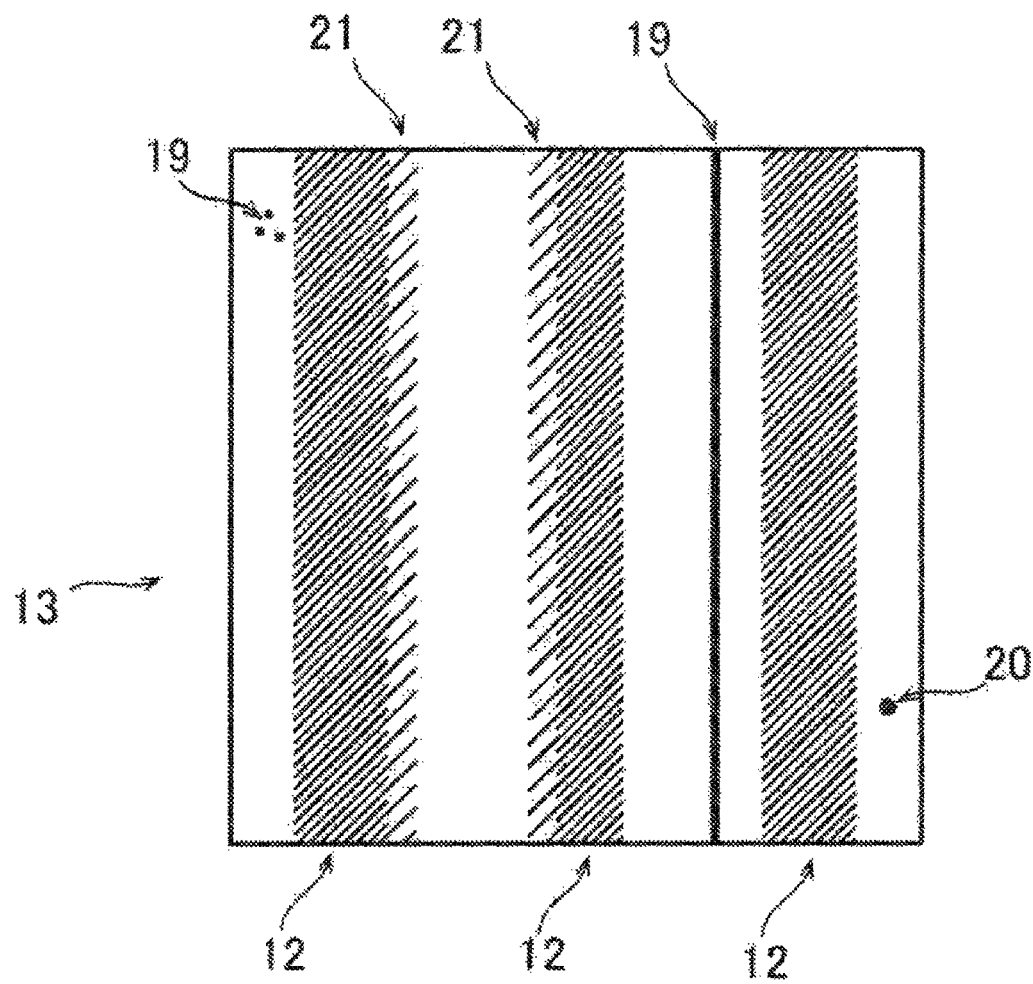
FIG. 17 is a schematic diagram of an interference fringe image in which noise is generated.

Here, in the case where a pixel defect occurs in the detector 5 or a defect occurs in the first grating 3 and/or the second grating 4, as shown in FIG. 17, in the interference fringe image 13, the noise 19 due to the pixel defect of the detector 5, the noise 20 due to the defect of the grating, etc., are observed. Further, when sensitivity unevenness corresponding to the incident angle occurs in the detector 5 due to the X-ray incident in the oblique direction against the grating, sensitivity unevenness 21 is observed in the interference fringe image 13.

Figure 18:
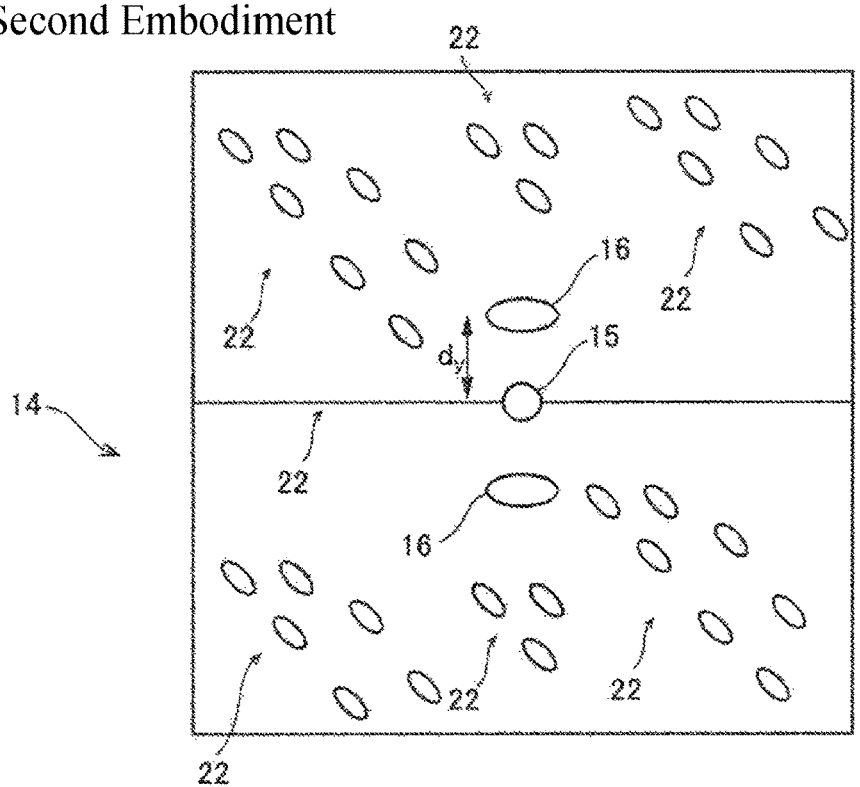
FIG. 18 is a schematic diagram of a Fourier transform image in which noise is generated.

When the interference fringe image 13 as shown in FIG. 17 is Fourier transformed, as shown in FIG. 18, peaks other than the zero-order peak 15 and the first-order peak 16 occur in the Fourier transform image 14 as noise 22. The noise 22 occurring in the Fourier transform image 14 is generated by the direction in which the X-ray source 1 is installed or the defects of a plurality of grating and detector 5 themselves. Therefore, unlike random noise, the position where the noise 22 occurs in the Fourier transform image 14 and the Fourier transform reference image 23 is substantially identical.

Figure 19:
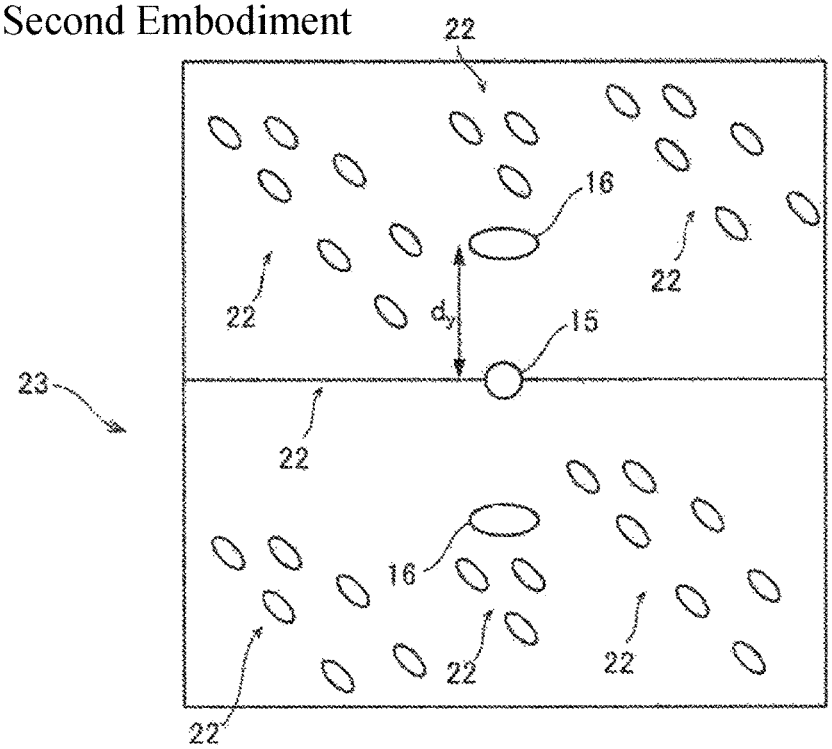
FIG. 19 is a schematic diagram of a Fourier transform reference image.

Under the circumstance, in the second embodiment, as shown in FIG. 19, the image processing section 10 is configured to eliminate the noise 22 generated in the Fourier transform image 14 using the Fourier transform reference image 23 previously obtained by Fourier transforming the interference fringe image 13.

Figure 20:
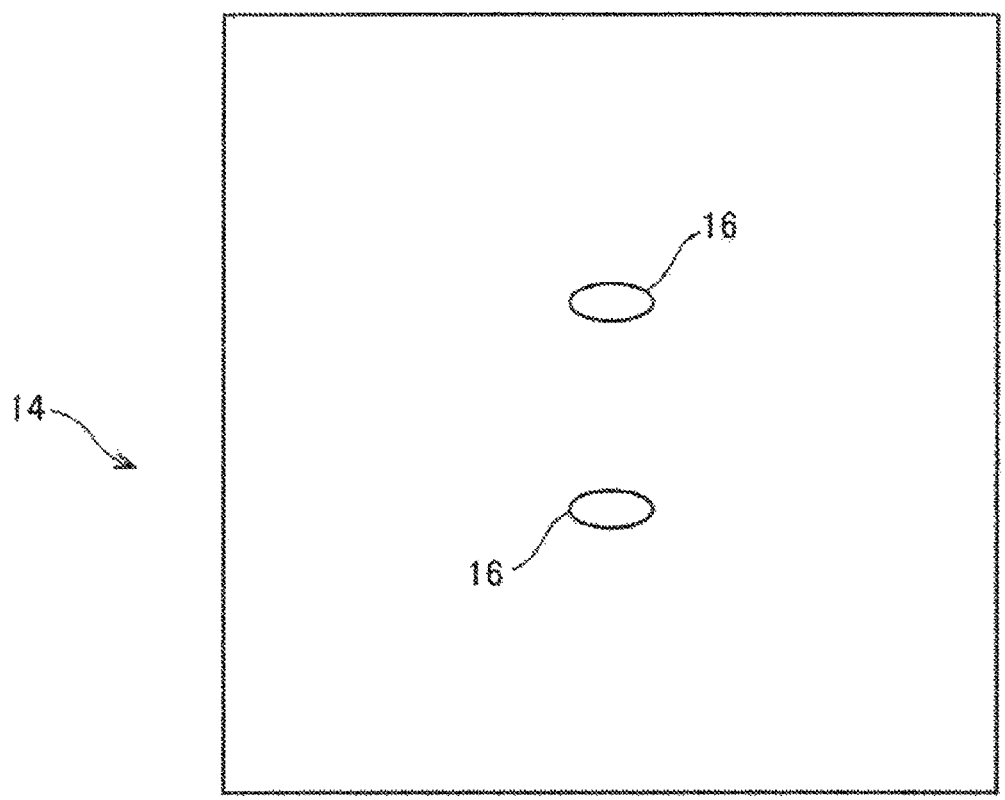
FIG. 20 is a schematic diagram of a noise-removed Fourier transform image.

Concretely, the image processing section 10 is configured to eliminate the noise 22 by subtracting the Fourier transform reference image 23 from the Fourier transform image 14. Unlike random noise, the noise 22 does not substantially change in position in the Fourier transform image 14 and Fourier transform reference image 23. Therefore, by subtracting the Fourier transform reference image 23 from the Fourier transform image 14, the noise 22 can be eliminated. As shown in FIG. 20, only the first-order peak 16 is observed in the Fourier transform image 14 after the noise 22 is eliminated.

In the case where the position of the first-order peak 16 in the Fourier transform image 14 and the position of the first-order peak 16 in the Fourier transform reference image 23 overlap, the first-order peak 16 is also eliminated together with the noise 22 by subtracting, it becomes impossible to observe the first-order peak 16 in the Fourier transform image 14.

Therefore, as shown in FIG. 19, the Fourier transform reference image 23 is an image which is difference from the Fourier transform image 14 in the position of the first-order peak 16. Specifically, in the example shown in FIG. 19, the first-order peak 16 of the Fourier transform reference image 23 is an example of an image in which the distance $d_y$ to the zero-order peak 15 is larger than the first-order peak 16 in the Fourier transform image 14.

The position of the first-order peak 16 observed in the Fourier transform image 14 and the Fourier transform reference image 23 is based on the period of the moire fringe 12. Therefore, by moving at least one of a plurality of gratings to change the period of the moire fringe 12, the position of the first-order peak 16 observed in the Fourier transform image 14 (Fourier transform reference image 23) can be changed.

Further, the Fourier transform reference image 23 may be acquired at any time before performing the grating position adjustment. For example, the previously acquired Fourier transform reference image may be stored in a storage (e.g., a hard disk or other computer memory—not shown) or the like and read out from the storage when acquiring the Fourier transform image 14, or may be acquired every time the grating position adjustment is performed. However, when a long period of time has passed after acquiring the Fourier transform reference image 23, there is a possibility that the pixel defects of the detector 5, defects of the grating, etc., increase, the noise 22 generated in the Fourier transform image 14 may be different from the noise 22 generated in the Fourier transform reference image 23 in some cases. Therefore, the Fourier transform reference image 23 is preferably acquired before the Fourier transform image 14 is acquired each time the position adjustment of the grating is performed.

Figure 21:
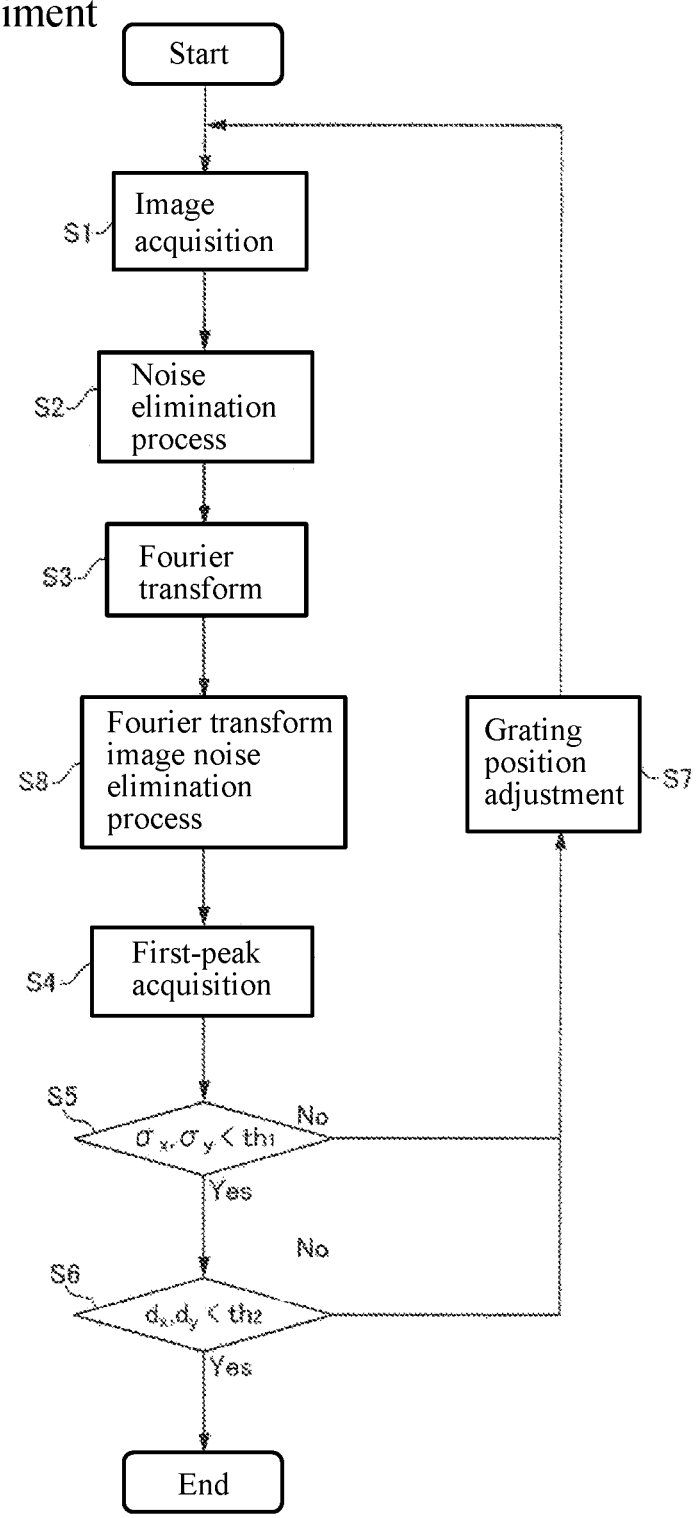
FIG. 21 is a flowchart for adjusting a positional displacement of a grating in the X-ray phase contrast imaging system according to the first embodiment of the present invention.

Next, with reference to FIG. 21, the overall flow of the method of adjusting the grating by the X-ray phase contrast imaging system 200 in the second embodiment will be described. Since the processing of Steps S1 to S7 is similar to that of the first embodiment, the detailed description thereof will be omitted.

In Steps S1 to S3, the X-ray phase contrast imaging system 200 acquires the Fourier transform image 14. Thereafter, in Step S8, the image processing section 10 subtracts the Fourier transform reference image 23 from the Fourier transform image 14, thereby eliminating the noise 22 generated in the Fourier transform image 14.

Thereafter, the processing proceeds from Step S4 to Step S5. When no positional displacement of the grating exists, the process proceeds to Step S6, and the process is terminated. When there exists a positional displacement of the grating, the process proceeds to Step S7, and the control section 9 performs position adjustment of the grating. Then, the process proceeds to Step S1.

Other configurations of the second embodiment are the same as those of the first embodiment.

Effects of Second Embodiment

In the second embodiment, the following effects can be obtained.

In the second embodiment, as described above, an image processing section 10 for eliminating the noise 22 to be generated in the Fourier transform image 14 by using the Fourier transform reference image 23 previously obtained by Fourier transforming the interference fringe image 13 is further provided. This makes it possible to eliminate the noise 22 to be generated in the Fourier transform image 14, so it is possible to accurately acquire the position and/or the magnitude of the first-order peak 16. As a result, it is possible to detect the peaks due to the positional displacement of the grating obtained by the Fourier transform more accurately, so that the accuracy of adjusting the positional displacement of the grating can be enhanced.

Further, in the second embodiment, as described above, the image processing section 10 is configured to eliminate the noise 22 by subtracting the Fourier transform reference image 23 from the Fourier transform image 14. With this, unlike random noise, the noise 22 of the Fourier transform image 14, which is less likely to be changed with time, can be easily eliminated.

Further, in the second embodiment, as described above, the Fourier transform reference image 23 is an image which is difference from the Fourier transform image 14 in the position of the first-order peak 16. By using such an image, when eliminating the noise 22 of the Fourier transform image 14, the first-order peak 16 of the Fourier transform reference image 23 can be suppressed from being eliminated together with the noise 22 by the first-order peak 16 in the Fourier transform image 14. As a result, the noise 22 of the Fourier transform image 14 can be eliminated regardless of the position of the first-order peak 16 in the Fourier transform image 14.

Other effects of the second embodiment are the same as those of the first embodiment.

Modified Embodiments

It should be understood that the embodiments disclosed here are examples in all respects and are not restrictive. The scope of the present invention is shown by the scope of the claims rather than the descriptions of the embodiments described above, and includes all changes (modifications) within the meaning of equivalent and the scope of claims.

For example, in the first and second embodiments, the phase grating is used as the first grating 3, but the present invention is not limited to this. For example, an absorption grating may be used as the first grating 3. As a result, even in the configuration of either one of the the interferometer and the non-interferometer, it becomes possible to perform X-ray phase contrast image capturing, which can enhance the degree of freedom in selecting the first grating 3.

Further, in the first and second embodiments, the example in which the third grating 2 is provided is shown, but the present invention is not limited thereto. For example, when the coherence of the X-ray source 1 is sufficiently high, it is not necessary to provide the third grating 2.

Further, in the first and second embodiments, the example in which the control section 9 generates the Fourier transform image 14, but the present invention is not limited thereto. For example, the image processing section 10 may be configured to generate a Fourier transform image 14.

Further, in the first and second embodiments, an example in which the magnitude of the zero-order peak 15 and the magnitude of the first-order peak 16 are determined by the half-value width of the frequency peak after the Fourier transform, but the present invention is not limited thereto. For example, the magnitude other than the half-value width of the frequency peak after the Fourier transform may be used. For the magnitude other than the half-value width, for example, the magnitude of the width of the frequency peak that is 40% of the maximum amplitude of the frequency peak after the Fourier transform may be used as the magnitude of the zero-order peak 15 and the first-order. Also, the respective areas of the zero-order peak 15 and the first-order peak 16 of the Fourier transform image 14 may be used as the magnitude of each peak.

Figure 22:
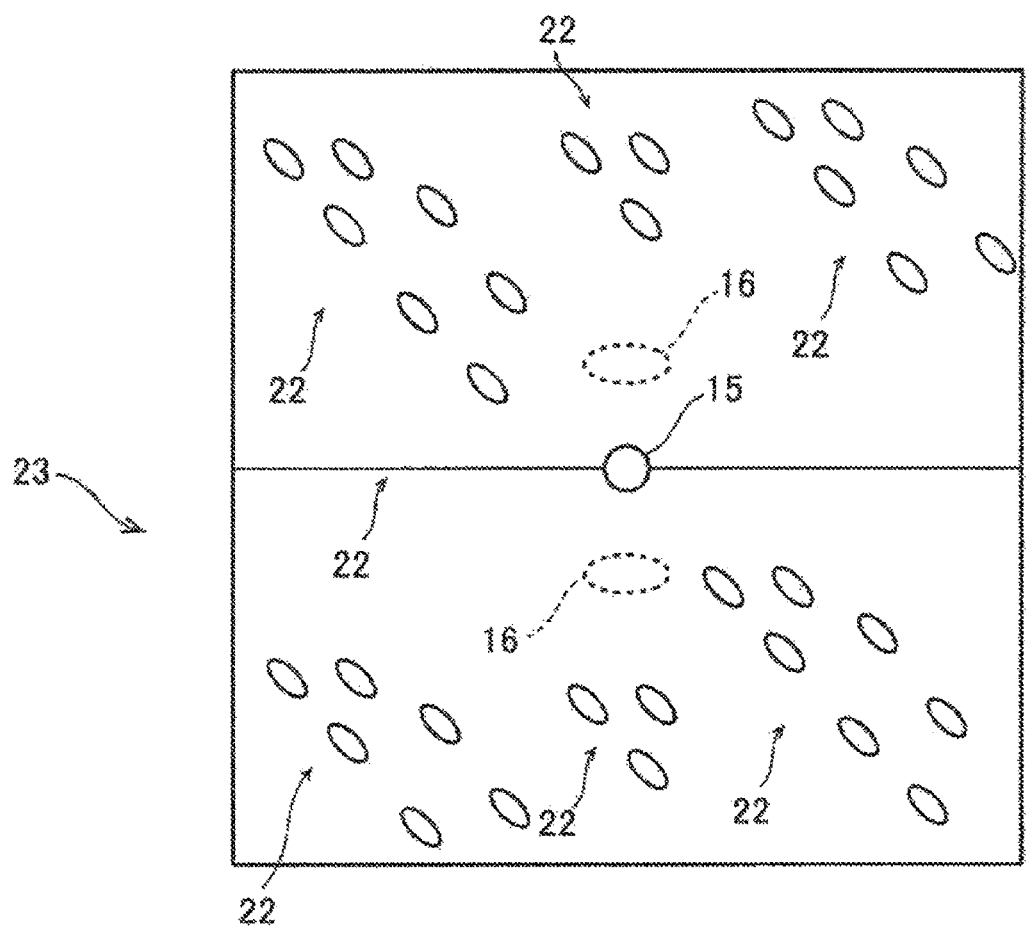
FIG. 22 is a schematic diagram of a Fourier transform reference image generated by the image processing section 10 according to a modification of the second embodiment.

Further, in the second embodiment, an example in which the Fourier transform reference image 23 having the first-order peak 16 in the position different from the position of the first-order peak 16 in the Fourier transform image 14 is shown, but the present invention is not limited thereto. For example, even when the position of the first-order peak 16 in the Fourier transform image 14 and the position of the first-order peak 16 in the Fourier transform reference image 23 overlap, as shown in FIG. 22, the image processing section 10 may be configured to eliminate the noise 22 of the Fourier transform image 14 using the Fourier transform reference image 23 obtained by eliminating the first-order peak 16 of the Fourier transform image 14. In the example shown in FIG. 22, the first-order peak 16 eliminated for the sake of convenience is indicated by a broken line.

The invention claimed is:

1. An X-ray phase contrast imaging system comprising:
   an X-ray source;
   a detector configured to detect an X-ray irradiated from the X-ray source;
   a plurality of gratings disposed between the X-ray source and the detector, the plurality of gratings including a first grating for forming a self-image by being irradiated by the X-ray from the X-ray source and a second grating for forming an interference fringe with the self-image of the first grating by being irradiated by the X-ray that has passed through the first grating; and
   a grating positional displacement acquisition section configured to acquire a positional displacement of at least one of the plurality of gratings based on one or more peaks of a Fourier transform image obtained by Fourier transforming an interference fringe image detected by the detector.

2. The X-ray phase contrast imaging system as recited in claim 1,
   further comprising an adjustment mechanism configured to adjust the positional displacement of at least either one of the first grating and the second grating,
   wherein the adjustment mechanism is configured to correct the positional displacement of at least one of the plurality of gratings based on the positional displacement of at least one of the plurality of gratings acquired by the grating positional displacement acquisition section.

3. The X-ray phase contrast imaging system as recited in claim 1,
wherein the grating positional displacement acquisition section is configured to acquire the positional displacement of at least one of the plurality of gratings based on at least either one of a peak-to-peak distance and a peak magnitude of the Fourier transform image.

4. The X-ray phase contrast imaging system as recited in claim 3,
wherein the grating positional displacement acquisition section is configured to acquire a positional displacement of the first grating or the second grating in an optical axis direction of the X-ray or a positional displacement of the first grating or the second grating in a rotational direction about the optical axis direction of the X-ray based on a distance between a zero-order peak and a first-order peak in the Fourier transform image.

5. The X-ray phase contrast imaging system as recited in claim 4,
wherein the grating positional displacement acquisition section is configured to acquire a magnitude of the positional displacement of at least one of the plurality of gratings based on the distance between the zero-order peak and the first-order peak in the Fourier transform image.

6. The X-ray phase contrast imaging system as recited in claim 3,
wherein the grating positional displacement acquisition section is configured to acquire the positional displacement of the first grating or the second grating in a rotational direction about a central axis of a vertical direction or a horizontal direction orthogonal to an optical axis direction of the X-ray of the first grating or the second grating based on a magnitude of a first-order peak in the Fourier transform image.

7. The X-ray phase contrast imaging system as recited in claim 6,
wherein the grating positional displacement acquisition section is configured to acquire presence or absence of a positional displacement of at least one of the plurality of gratings based on the magnitude of the first-order peak in the Fourier transform image.

8. The X-ray phase contrast imaging system as recited in claim 7,
wherein the grating positional displacement acquisition section is configured to acquire a rotation amount that a magnitude of the first-order peak in the Fourier transform image becomes a minimum value or near the minimum value as a positional displacement amount based on a plurality of Fourier transform images captured by rotating either one of the first grating and the second grating.

9. The X-ray phase contrast imaging system as recited in claim 1, further comprising a noise elimination processing module configured to eliminate frequency noise from the image detected by the detector before performing the Fourier transforming.

10. The X-ray phase contrast imaging system as recited in claim 1, further comprising an image processing module configured to eliminate noise generated in the Fourier transform image by using a Fourier transform reference image previously obtained by Fourier transforming the interference fringe image.

11. The X-ray phase contrast imaging system as recited in claim 10,
wherein the image processing module is configured to eliminate the noise by subtracting the Fourier transform reference image from the Fourier transform image.

12. The X-ray phase contrast imaging system as recited in claim 10,
wherein the Fourier transform reference image is an image which is different from the Fourier transform image in a position of first-order peak or an image obtained by eliminating the first-order peak of the Fourier transform image.

* * * * *